(12) United States Patent
Drasler et al.

(10) Patent No.: US 9,511,209 B2
(45) Date of Patent: Dec. 6, 2016

(54) BULBOUS BALLOON WITH MECHANICAL PRESSURE REGULATOR

(71) Applicant: InterValve, Inc., Minnetonka, MN (US)

(72) Inventors: William J. Drasler, Minnetonka, MN (US); Mark Ungs, Minnetonka, MN (US); Wesley R. Pedersen, Minneapolis, MN (US)

(73) Assignee: InterValve, Inc., Minnetonka, MN (US)

( * ) Notice: Subject to any disclaimer, the term of this patent is extended or adjusted under 35 U.S.C. 154(b) by 187 days.

(21) Appl. No.: 14/452,426

(22) Filed: Aug. 5, 2014

(65) Prior Publication Data

US 2015/0045826 A1    Feb. 12, 2015

Related U.S. Application Data

(60) Provisional application No. 61/862,908, filed on Aug. 6, 2013, provisional application No. 61/876,149, filed
(Continued)

(51) Int. Cl.
*A61M 29/00* (2006.01)
*A61M 29/02* (2006.01)
(Continued)

(52) U.S. Cl.
CPC ......... *A61M 29/02* (2013.01); *A61M 25/1002* (2013.01); *A61M 25/104* (2013.01); *A61M 25/1011* (2013.01); *A61F 2/2427* (2013.01); *A61M 25/1018* (2013.01); *A61M 25/10182* (2013.11); *A61M 25/10185* (2013.11);
(Continued)

(58) Field of Classification Search
CPC ............. A61M 2025/0002; A61M 2025/1031; A61M 2025/1047; A61M 2025/1075; A61M 2025/1086; A61M 2025/1088; A61M 25/1002; A61M 25/1011; A61M 25/1018; A61M 2025/1013; A61M 2025/1079; A61M 25/10; A61M 25/10182; A61B 17/22012; A61B 2017/22098; A61B 2018/00422; A61B 2018/00577; A61F 2/2427
(Continued)

(56) References Cited

U.S. PATENT DOCUMENTS

2006/0129093 A1    6/2006    Jackson
2010/0082012 A1    4/2010    Hattangadi et al.
(Continued)

OTHER PUBLICATIONS

WIPO, U.S. International Search Authority, International Search Report and Written Opinion of Patentability mailed Dec. 11, 2014 in International Patent Application PCT/US2014/049818, 8 pages.

*Primary Examiner* — Katherine M Shi
(74) *Attorney, Agent, or Firm* — Inskeep IP Group, Inc.

(57) ABSTRACT

A measuring balloon has an inner bulbous balloon formed from a non-compliant or semi-compliant material and has a central smaller diameter inner waist and two larger diameter bulbs on each side of the inner waist. A compliant outer waist bladder is located on the outside of the inner bulbous balloon adjacent to the inner waist and is inflated via a separate inflation lumen. The inner balloon is inflated at a higher pressure to dilate stenotic aortic valve leaflets, and provide alignment and positioning of the measuring balloon across the aortic annulus. The bladder waist is inflated to a lower pressure to make contact with the aortic valve annulus. Marker bands positioned on the outside of the measuring balloon provide determination of annulus diameter and ovality.

18 Claims, 22 Drawing Sheets

Related U.S. Application Data on Sep. 10, 2013, provisional application No. 61/894,723, filed on Oct. 23, 2013, provisional application No. 61/915,447, filed on Dec. 12, 2013, provisional application No. 61/947,845, filed on Mar. 4, 2014, provisional application No. 61/986,743, filed on Apr. 30, 2014.

(51) Int. Cl.
*A61M 25/10* (2013.01)
*A61M 25/00* (2006.01)
*A61F 2/24* (2006.01)

(52) U.S. Cl.
CPC ........... *A61M 2025/0002* (2013.01); *A61M 2025/1013* (2013.01); *A61M 2025/1031* (2013.01); *A61M 2025/1047* (2013.01); *A61M 2025/1075* (2013.01); *A61M 2025/1079* (2013.01); *A61M 2025/1086* (2013.01); *A61M 2025/1088* (2013.01)

(58) Field of Classification Search
USPC ............................... 604/101.02; 606/194, 21
See application file for complete search history.

(56) References Cited

U.S. PATENT DOCUMENTS

| | | | |
|---|---|---|---|
| 2010/0094209 A1* | 4/2010 | Drasler | A61M 25/1002 604/95.04 |
| 2011/0144742 A1* | 6/2011 | Madrid | A61F 2/2433 623/2.11 |
| 2012/0143131 A1 | 6/2012 | Tun et al. | |
| 2012/0277785 A1 | 11/2012 | Aggerholm et al. | |
| 2014/0012304 A1* | 1/2014 | Lampropoulos | A61M 25/10 606/192 |

\* cited by examiner

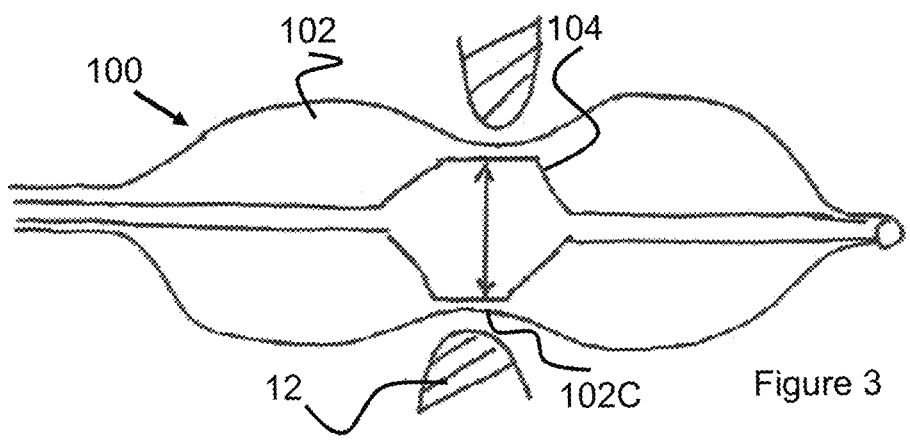
Figure 3
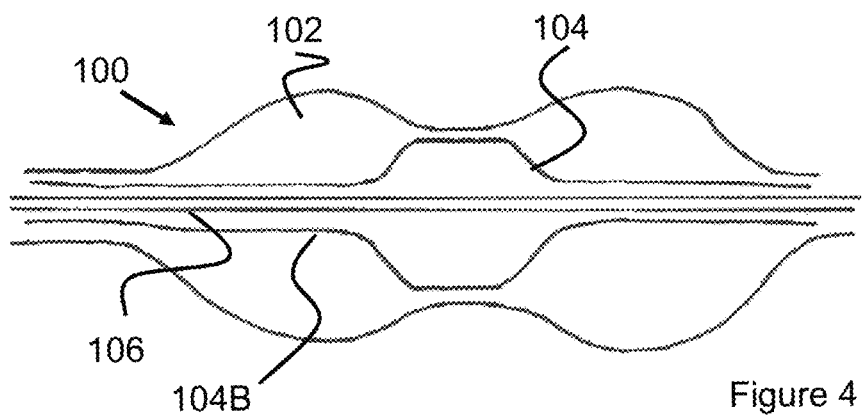
Figure 4
Figure 5
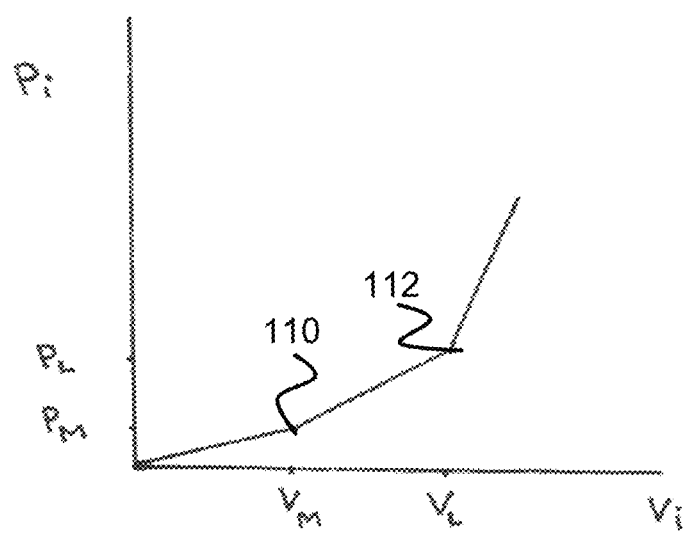

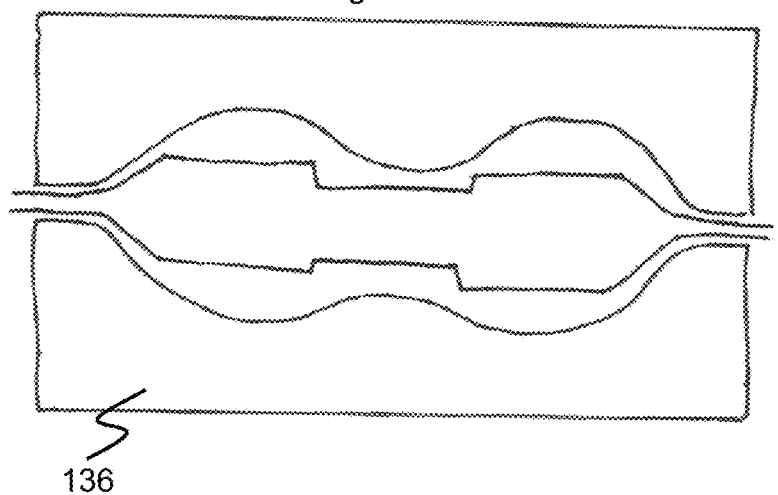
Figure 13
136
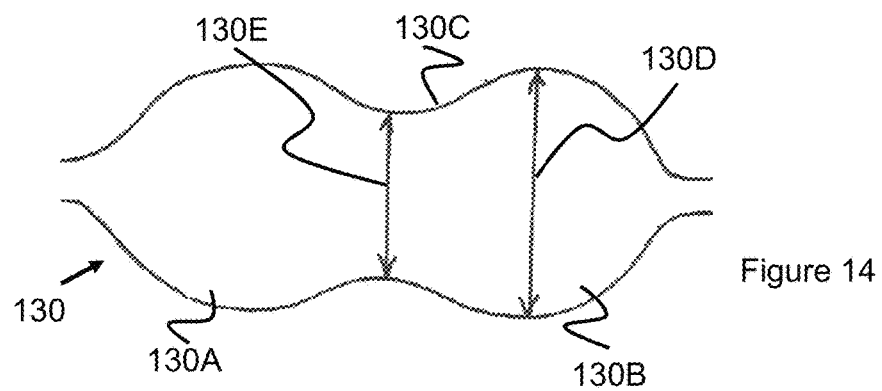
Figure 14
130E  130C  130D
130
130A  130B
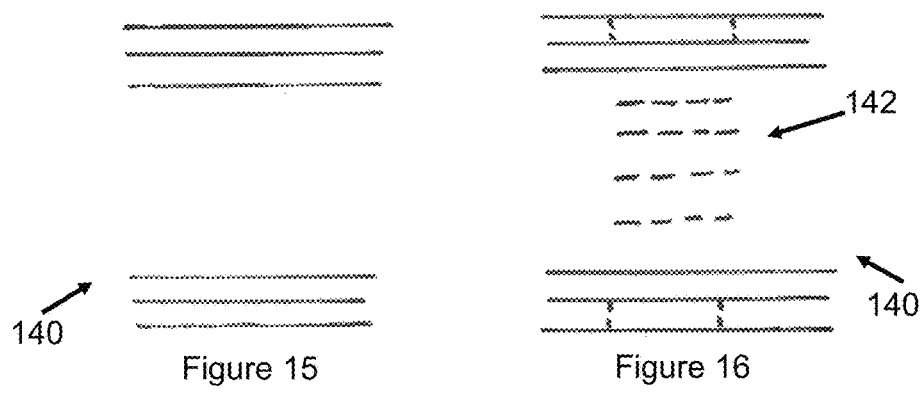
140
Figure 15
142
140
Figure 16

Figure 33
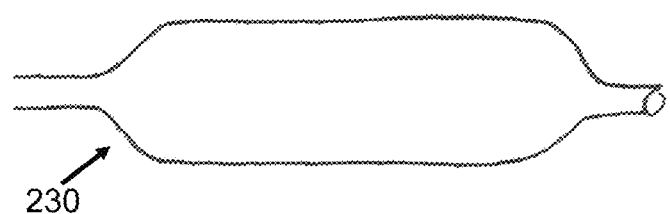
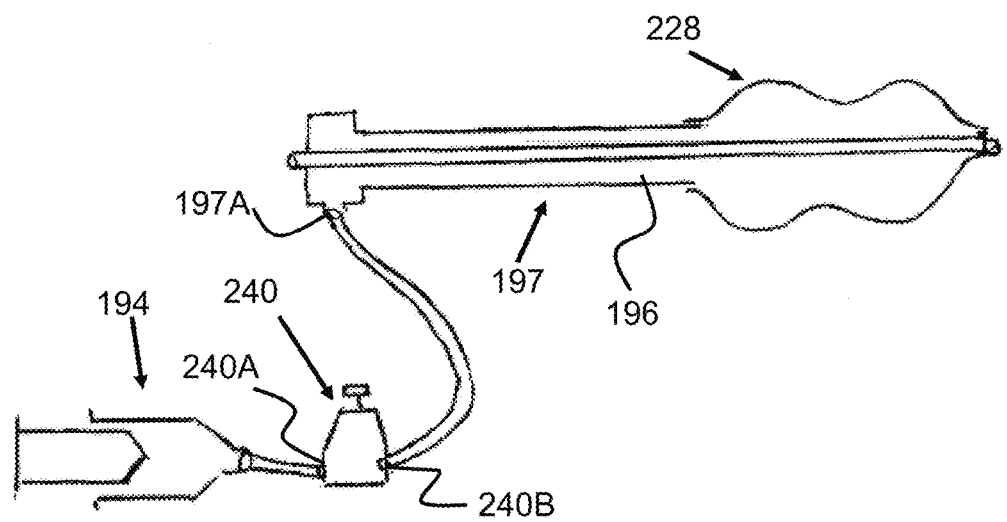
Figure 34

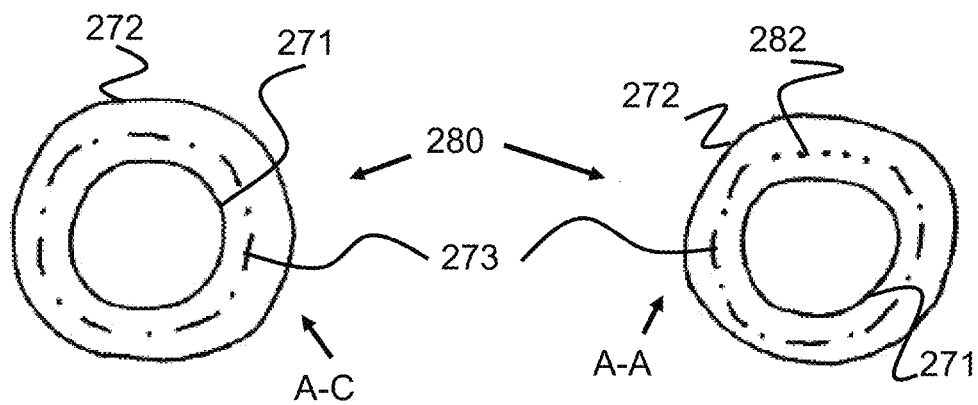
Figure 39E  Figure 39C
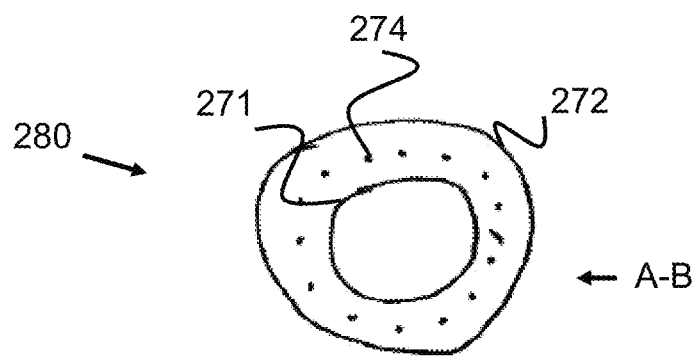
Figure 39D
Figure 40A
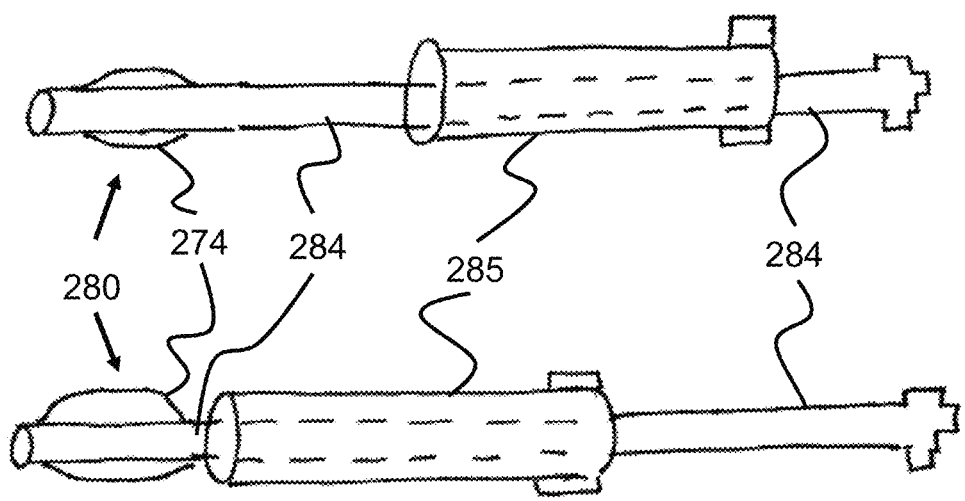
Figure 40B 285    284

BULBOUS BALLOON WITH MECHANICAL PRESSURE REGULATOR

RELATED APPLICATIONS

This application claims priority to U.S. Provisional Application Ser. No. 61/862,908 filed Aug. 6, 2013 entitled Bulbous Balloon For Annulus Measurement, U.S. Provisional Application Ser. No. 61/876,149 filed Sep. 10, 2013 entitled Bulbous Balloon For Annulus Measurement, U.S. Provisional Application Ser. No. 61/894,723 filed Oct. 23, 2013 entitled Bulbous Balloon With Pressure Control Assembly Device And Method, U.S. Provisional Application Ser. No. 61/915,447 filed Dec. 12, 2013 entitled Bulbous Balloon With Waist Bladder For Diameter Measurement, U.S. Provisional Application Ser. No. 61/947,845 filed Mar. 4, 2014 entitled Bulbous Balloon With Mechanical Pressure Regulator, and U.S. Provisional Application Ser. No. 61/986,743 filed Apr. 30, 2014 entitled Bulbous Balloon For Annulus Measurement, all of which are hereby incorporated herein by reference in their entireties.

BACKGROUND OF THE INVENTION

U.S. Pat. No. 7,951,111 is hereby incorporated by reference in its entirety.

A bulbous balloon can be used to perform a therapeutic valvuloplasty procedure on a native valve of the heart; the same balloon can then be used diagnostically to provide measurements of the diameter of the valve annulus. An accurate measurement of the annulus can enable a proper sizing of a transcatheter aortic valve replacement (TAVR) device such that valve migration and leakage around the valve are mitigated.

SUMMARY OF THE INVENTION

The present application describes the bulbous and cylindrically shaped balloon and methods for making the balloon and using it to measure the diameter of an annulus of a valve of the body, and more specifically the aortic valve annulus diameter. The balloon is used for performing a valvuloplasty therapeutic procedure on a valve of the body followed by a diagnostic measurement of the annulus diameter in a stretched configuration.

In one embodiment the balloon used to measure the diameter of the aortic annulus can be formed from two balloons, an outer bulbous balloon and an inner balloon placed within the outer balloon. The outer balloon can be formed from a semi-compliant material such as Pebax or Nylon that allows for expansion of the balloon waist under increasing pressure or volume injected into the balloon. It is of benefit to the accurate measurement capability of the present invention to restrict the bulb portions of the balloon from increase in diameter and thereby enhance the ability to observe a change in slope of the pressure versus volume curve as the waist makes contact with the annulus.

To help improve the observation of a slope change during annulus contact by the waist, a second balloon is placed inside of the bulbous balloon. This inner balloon is smaller in length than the larger bulbous outer balloon and is located mainly adjacent to the waist of the outer balloon either touching it or initially spaced apart from it prior to full inflation. The volume of the inner balloon is significantly smaller than that of the outer balloon so that the observed slope change of the Pressure versus Volume for the inner balloon is maximized. The inner balloon can be either a non-compliant balloon that has a native or natural diameter under zero or low pressure (approximately 0.25 atm) that is larger than the waist of the outer balloon by 2-6 mm and can enlarge to a fully inflated diameter that is approximately 2-6 mm larger than the outer balloon waist diameter. Alternately the inner balloon can be formed from a semi-compliant material and can have a native diameter equal or smaller than the outer balloon waist diameter and can grow in diameter to contact and push the waist outward to a larger diameter by 3-6 mm at increasing pressures.

Through monitoring of the change in pressure within the inner balloon along with the change in volume injected within the inner balloon, a slope change in a pressure versus balloon volume curve will first be observed when the inner balloon makes contact with the waist of the outer balloon. A second slope change will also be observed when the outer balloon makes contact with the annulus and expands the annulus into a circular shape that represents the perimeter of the annulus. When the waist of the outer balloon is in full contact along the perimeter of the annulus, an inflection point will be observed in the delta P within the inner balloon versus delta V of the inner balloon curve; it is at this point that standard imaging techniques can be used to identify the diameter of the annulus. Monitoring the pressure and volume of the inner balloon rather than the outer balloon allows enhancement of the slope change at the inflection point independent of growth of the bulbs of the outer balloon.

An alternate bulbous balloon formed from only a single contained balloon space can also be used to identify the diameter of the valve annulus. To form a bulbous balloon that has generally non-compliant bulbs and yet allows for significant expansion of the waist to make contact with the annulus can be accomplished via methods described herein. The non-compliant bulbs or significantly limited expansion semi-compliant bulbs are necessary to provide an increase in observable slope change of the delta Pressure versus delta Volume curve with the balloon when the waist of the balloon makes contact with the annulus and which is indicative of the diameter of the annulus.

One method for forming such a balloon is to first form a cylindrical balloon from a single extrusion of plastic or a coextrusion of two plastics (or multiextrusion if desired). One example would be to extrude Nylon over Pebax to form a coextrusion. The extruded tubing is sized to form a bulbous balloon with bulb diameters that range, for example from 22-30 mm. The cylindrical balloon that is first formed from the tubing could initially be formed at a diameter that is less than its sized bulb diameter by approximately 4-6 mm and could be similar to the diameter of the waist of the bulbous balloon. The waist of the balloon ranges from approximately 2-10 mm less than the diameter of the bulbs.

The region of the cylindrical balloon that is intended to be formed into a waist region for a bulbous balloon could be exposed to a variety of processing methods to either weaken or ablate material from the waist region. For example, a laser could be used to remove the outer layer of a coextruded balloon wall such that only the inner layer remains. Alternately, the laser can be used to remove a portion of a single extrusion of material in the waist region. The wall thickness, for example in the waist could be 0.002-0.006 inches and half of that thickness, for example could be removed via a laser ablation. Further alternately, axial slits can be cut through a portion of the wall thickness of the waist region. The waist region could have a length, for example of 3-15 mm and lie generally in the middle of the balloon between the two ends.

Once the waist region of the cylindrical balloon has been ablated or weakened via slits or other means, the balloon can then be further inflated within a balloon mold under pressure and increased temperature to cause the bulbous portions of the balloon to be formed.

Alternately, the final bulbous shaped balloon can be ablated or weakened within the waist region to allow the waist to expand outwards against the annulus under increasing pressure while the bulbous regions behave substantially as a non-compliant material. Such non-compliant behavior for the bulbs must allow for minimal diameter change of the bulbs with increasing pressure as the waist comes into contact with the annulus. The diameter change for the bulbs, for example, should be less than approximately 0.5 mm/atm of inflation pressure.

In yet another embodiment, a single or coextrusion of two plastic materials can be ablated or slit axially in the future waist region prior to forming a bulbous balloon. Such processing of the tubing is more repeatable for laser ablation due to the larger wall thicknesses for the tubing prior to forming the balloon and due to the more consistent cylindrical shape of an extruded tubing in comparison to a balloon. Processing of the balloon formed from ablated tubing using standard balloon blowing techniques, however, will require some adjustment to place the weakened or ablated region into a correct location for the balloon waist.

In one embodiment of the present invention a bulbous balloon having a semi-compliant waist and non-compliant bulbs is used to form a therapeutic dilation of the leaflets with the bulbs while the waist remains at a similar diameter or smaller diameter than the annulus. Following the therapeutic procedure, the balloon is exposed to a higher volume of inflation fluid thereby causing the pressure inside the balloon to increase causing the waist to come into contact with the annulus. At the contact point, the pressure within the balloon will rise at a rate that is greater than the pressure versus volume compliance curve for the balloon in free space. Upon injection of additional volume, the internal pressure within the balloon rises to a set pressure or spill-off pressure which is higher than the internal pressure would be if the balloon were inflated in free space according to the balloon compliance curve. Any extra inflation fluid injected above this additional volume will be spilled off by a pressure relief valve. The presence of a spilled off volume that is above that which would be expected for the balloon in free space for that extra volume injected is indicative that the waist has made contact with the annulus. One can thereby ensure through examination of the fluoroscopy image that the balloon waist has made contact with the annulus and will reflect the diameter of the annulus.

The force that the semi-compliant waist applies to the annulus is less than that associated with the internal balloon pressure. The semi-compliant waist provides a restraining force that matches the forces provided by the internal balloon pressure at the time the waist makes contact with the annulus. Application of a greater internal pressure will apply a force outwards against the annulus equal to the internal pressure within the balloon minus the restraining force provided by the balloon when it first made contact with the annulus.

The accuracy of the diameter measurements using fluoroscopy can be affected by the orientation of the balloon with respect to the angle of the fluoroscopy camera. Radiopaque markers can be placed around the perimeter of the waist and/or bulb to provide assurance that the balloon has been aligned perpendicular to the fluoroscopy camera. Also, such circumferentially oriented marker bands can locate the position of the annulus along the axis of the aortic root as well as align the TAVR axis with respect to the axis of the aortic root.

Several balloon structures can be employed to provide the semi-compliant waist and non-compliant bulbs of the present invention. In one embodiment a balloon is formed from a semi-compliant material such as Pebax or a semi-compliant lower durometer Nylon and fibers can be placed in the bulb areas that restrict the diametric growth of the bulbs under increasing pressure or volume relative to the waist diametric growth. The fibers can be a braid, a weave, or a spiral wind of a fiber that has a high tensile force. Such fibers include ultra-high molecular weight polyethylene (UHMWPE), Dacron, Kevlar, and other fibers used in the medical device industry.

Alternately the balloon structure can include a wall thickness for the balloon that has been thinned down or weakened in the waist region of the balloon. The wall can be formed from one, two, or more separate layers of material and one or more layers can be ablated or removed from the balloon using mechanical, laser, or other methods to provide the waist with greater compliance ability to expand outwards under pressure relative to the non-compliant bulbs. A bulbous balloon formed from a single semi-compliant (sc) material, such as a Pebax, Nylon, or polyurethane material.

In still another embodiment a bulbous balloon can be used to therapeutically dilate the leaflets and diagnostically measure the diameter of annulus using a spill-off valve to control the pressure or volume delivery to the balloon such as that described earlier. The spill-off pressure can be set, for example, to 2 atmospheres. This embodiment can have an outer bulbous balloon and a smaller cylindrical inner balloon contained with it. The inner balloon is located adjacent to the waist of the outer bulbous balloon. Following the therapeutic dilation of the leaflets via the outer balloon or both balloons together, a specified volume is injected (for example, during a second injection) into the outer balloon to position the balloons properly with the waist of the outer balloon adjacent the annulus. Additional volume is then injected into the inner balloon in accordance with a compliance curve that is primarily directed at the pressure versus volume compliance of the inner balloon along with the waist of the outer balloon. A spill-off pressure (ie., approximately 2 atm) is set and a compliance curve volume is injected into the inner balloon in accordance with the compliance curve that would attain the spill-off pressure of the inner balloon in free space. If the waist region of the outer balloon comes into contact with the annulus, the pressure within the inner balloon rises at a rate that is higher than its compliance curve and a fraction of the volume injected is spilled off and does enter into the balloon. The presence of this spill-off volume indicates that the waist has made contact with the annulus. Fluoroscopy can be used to measure the diameter of the annulus which has been placed into contact and stretched into a round shape by the waist of the inner balloon.

A pressure control assembly, PCA, is used to provide a pressure relief when a set pressure has been attained can. In one embodiment the pressure control assembly is a pressure relief valve that is attached to the manifold of the catheter or the delivery device or syringe. The pressure at the proximal end of the balloon inflation lumen is monitored either mechanically or electrically and a valve is opened if the pressure exceeds a set spill-off pressure.

In another embodiment the PCA can have a pressure transducer or pressure monitoring means to ensure that a pressure spike generated by uneven or rapid fluid delivery via a syringe does not cause unwarranted spill-off of injected fluid volume from the syringe, since the higher pressure spike does not reflect the actual pressure within the balloon. Adjustment for this pressure spike can be accomplished, for example, by providing the PCA with both a primary pressure relief valve that has a pressure attenuation resistance and a secondary sliding valve that is triggered by the primary pressure relief valve but can ensure that the syringe or balloon inflation lumen do not exceed a set spill-off pressure.

As a further embodiment, the pressure that is used to trigger the pressure relief valve can be obtained directly from within the balloon. The pressure can be sensed via an electrical pressure transducer or it can be obtained from a separate pressure sensing lumen that extends from the catheter manifold to the interior of the balloon. The pressure signal received from the pressure sensing lumen can be used to trigger a pressure relief valve which ensures that no further volume is delivered from the syringe to the balloon inflation lumen. Additionally, the pressure signal from the balloon ensures that the volume spill-off does not occur due to a high pressure spike due to rapid or uneven fluid injection from the syringe.

A yet further embodiment for the PCA includes a bladder assembly that is in fluid communication with the syringe or balloon inflation lumen. Injection of fluid from the syringe with a spike in pressure will be dampened by the bladder such that a pressure relief valve would not be triggered by such a spike.

A totally semi-compliant balloon having a bulbous shape or having a standard cylindrical shape can also be used with the spill-off methods and the pressure relief valve described in the present invention. Each of these types of balloons will have a specific pressure versus volume compliance curve that is followed via inflation in free space. If a portion of the balloon is constrained by an external structure such as the annulus of a heart valve, the pressure will be higher at a specific volume of inflation. Setting a spill-off pressure and then injecting a volume into the balloon that corresponds to the balloon volume at that pressure as per the compliance curve will not result in any spill-off volume in free space. If volume is spilled off, then it is known that a portion of the balloon has been restricted or placed into contact with an external structure of the body. If this structure is the annulus, then one can use fluoroscopy to visualize the balloon and thereby measure the diameter of the annulus. The spill-off volume will not be as great and not as easily observed in comparison to the bulbous balloon embodiment presented earlier having non-compliant bulbs and a semi-compliant waist; this is due to the ability of the totally semi-compliant balloon bulbs to expand in diameter during injection of inflation volume.

A noncompliant balloon having a bulbous shape or having a standard cylindrical shape can also be used with the spill-off methods and pressure relief valve described in the present invention. These balloons have been described in earlier embodiments of the present invention. The diameter of the bulbous balloon waist or the diameter of the cylindrical balloon would be made such that it had a diameter that was larger than the annulus. A specified fully inflated balloon volume for either balloon exists wherein its pressure may range from 0.5 to approximately 2 atm (as per the balloon volume inflation curve) and any further volume inflation will result in an exponential increase in balloon pressure with very little further volume injection until the balloon breaks. If one were to inject the balloon with inflation fluid to its fully inflated volume or less and observea pressure higher than expected from its pressure versus volume compliance curve then a pressure relief valve could be used to provide spill-off of volume above this pressure. Thus this balloon could be used to determine that it has made contact with the annulus and thereby use it to measure the diameter of the annulus. For this balloon the entire pressure found within the balloon is being placed upon the annulus and could lead to annular dissection if the pressure is set too high, for example, approximately 2 atm. Therefore, this embodiment is intended for diagnostic purposes alone rather than for therapeutic leaflet dilatation and diagnostic annular measurement if dilation of the leaflets requires a pressure within the balloon of greater than approximately 2 atm.

An alternate embodiment for the pressure control assembly utilizes a pressure regulator between an inflation device such as a syringe and the balloon inflation lumen. A specified volume of fluid is placed into the syringe that would allow the waist of the balloon to expand to a diameter larger than that during its initial contact with the valve annulus and would cause the pressure within the balloon in free space to achieve a specific set value. In accordance with the compliance curve for the balloon the pressure within the balloon would be above that required to dilate the leaflets (approx. 1.5-2.5 atm) and lower than the rated burst pressure of the balloon (approximately 3-4) atm, and lower than a pressure that could cause potential annular dissection (approximately 0.5-1.0 atm). The pressure regulator is set such that only a specific maximum pressure can be delivered to the balloon that corresponds to the pressure obtained from the compliance curve of the balloon at the specified volume described earlier when inflated in free space.

Injection of the specified volume of inflation fluid through the pressure regulator and into the balloon in free space will cause the balloon to reach a specific maximum pressure when all of the inflation fluid has exited the syringe. If, on the other hand, the waist of the balloon has come into contact with the valve annulus, then pressure at the outlet of the pressure regulator will reach the specific maximum pressure prior to delivery of all the fluid within the syringe. The presence of remaining fluid within the syringe will indicate to the physician that contact of the balloon waist has been made with the annulus. Edge to edge measurement of the balloon diameter under fluoroscopy will therefore reflect the diameter of the annulus.

The present use of a pressure regulator as a pressure control assembly can be applied to all of the balloon embodiments presented in the present invention. For example, the balloon can be formed from a single material such as a semi-compliant material such as Pebax or Nylon or others, and the balloon can have a cylindrical or bulbous shape as described earlier. Alternately, the balloon can be formed using any of the methods of construction described in this patent application such that the bulbous region of the balloon has a non-compliant character and the waist maintains a semi-compliant character. Other hydraulic and mechanical devices are presented that also serve as a pressure control assembly for use with the presently described method of use.

An alternate embodiment for dilation of stenotic aortic valve leaflets followed by measurement of an annulus diameter provides an inner bulbous balloon made out of a higher durometer polymeric material surrounded by a lower durometer or elastomeric polymeric bulbous balloon. The balloons are bonded together except for a region or waist bladder in the vicinity of the balloon waist. A separate inflation tube or channel is used to inflate the outer balloon in the waist region or waist bladder separately from the inflation of the inner balloon. The inflation channel can be a portion or a separate lumen of the inner bulbous balloon. The outer balloon can be a portion of a balloon that forms a waist bladder that is bonded to the inner balloon in the waist region of the inner balloon. The inner balloon can be made of a Nylon, higher durometer (i.e., 72D) Pebax, PET, or other balloon material that does not cause diametric growth of the bulb regions of the balloon by more than approximately 2 mm when inflated to pressures of 2 atm to approximately 3 atm. The inner balloon can be a dual lumen balloon formed from a dual lumen extrusion or it can be formed from a tri lumen or multi-lumen extrusion. The outer balloon material can be a softer or lower durometer Pebax, Polyurethane, composite, or other material that will grow in diameter of the waist by at least 3 mm (or more) at internal pressures of less than approximately 1 atm.

In use the inner balloon is inflated first with the waist adjacent the aortic annulus and the proximal bulb expands the stenotic aortic leaflets outwards into the aortic sinus region. Most aortic valve leaflets will expand outwards at pressures of approximately 2 atm. The waist of the balloon is not touching the annulus or at least not placing undue forces (i.e., force should be less than 1 atm) onto the annulus. Following leaflet expansion, the inner balloon is again inflated to approximately 2-3 atm, but in addition, the outer waist bladder is inflated at a low pressure of 0.25 to 2 atm such that the outer balloon waist makes definite contact with the annulus but does not impose significant stress onto the annulus that could cause annular dissection; less than 1 atm of stress should be applied to the annulus to ensure that it does not dissect.

The waist of the outer balloon can be filled with contrast medium such that fluoroscopy can be used to measure the diameter of the outer waist and hence the annulus. Alternately, a radiopaque ring can be placed around the outer waist of the outer balloon to better visualize the diameter of the annulus as well as provide information regarding orientation of the balloon. Alternately, an echogenic fluid such as a gas or a suspension of gas within a liquid can also be used to inflate the waist of the bladder.

In another embodiment an outer balloon of lower durometer polymer is again placed around an inner balloon of higher durometer polymer as described in the last embodiment. To ensure that the contrast medium that fills the waist bladder is not trapped within the bladder during evacuation, this embodiment provides for pushing the contrast medium out of the waist bladder when the balloon is pulled back out of the introducer sheath to exit the body.

In this embodiment a channel is formed in the distal bulb region between the inner and outer balloon. The channel is placed into fluid communication with the waist bladder and with an evacuation lumen that extends from the catheter manifold to the distal end of the catheter. Upon removal of the catheter from the introducer sheath, the contrast medium is squeezed out of the waist bladder, down the channel, and exits an evacuation opening into the evacuation lumen for removal at the catheter manifold. Alternately, an inlet and outlet lumen can be provided to ensure proper priming and evacuation of fluids from the waist bladder.

An alternate embodiment for a pressure control assembly can be a syringe that simulates a pressure regulator to deliver fluid to the catheter assembly at a controlled pressure that does not exceed a specified pressure. In this embodiment a spring located in the plunger of a syringe can be adjusted under compression to supply a pressure of approximately 2-3 atmospheres. If the specified pressure pushing against the plunger via the fluid is exceeded, a friction element moves to generate a frictional force that prohibits further movement of the plunger relative to the syringe barrel. This embodiment allows a compliant or semi-compliant waist of a balloon to expand outwards to make contact with the annulus of an aortic valve (to allow diameter measurement of the annulus under fluoroscopy, for example) but ensure that the outward force against the annulus is low enough such that the annulus does not dissect.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which FIGS. 1A, 1B, 2, 3, and 4 are various side views of a valvuloplasty balloon according to the present invention;

FIG. 5 is a graph showing a pressure vs. volume relationship for valvuloplasty balloons of the present invention;

FIGS. 10-14 are side views illustrating a manufacturing process for a valvuloplasty balloon according to the present invention;

FIGS. 15, 16, 17, 18, 19A and 19B are side views illustrating manufacturing processes for a valvuloplasty balloon according to the present invention;

FIG. 33 is a side view of a valvuloplasty balloon according to the present invention;

FIGS. 34 and 35 are various views of media inflation devices for inflating a balloon catheter according to the present invention;

FIGS. 38A, 38B, 39A, 39B, 39C, 39D, 39E, 40A, 40B, and 40C are side views of valvuloplasty balloons according to the present invention;

DESCRIPTION OF EMBODIMENTS

Figure 1A:
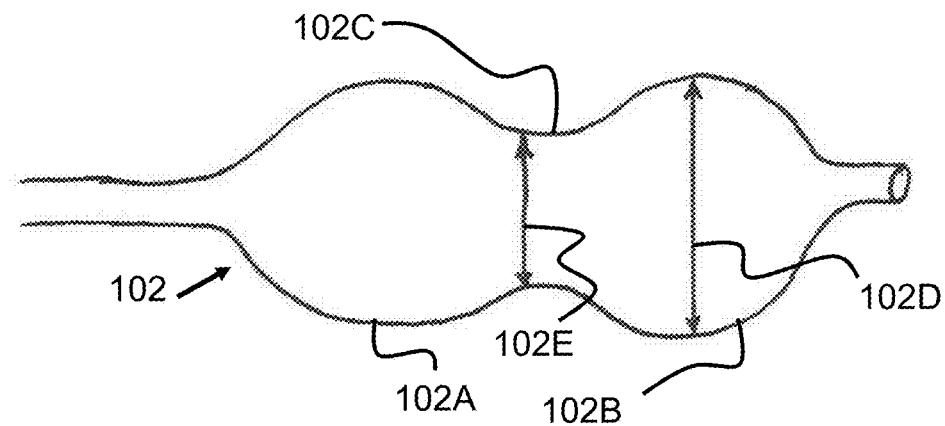

Specific embodiments of the invention will now be described with reference to the accompanying drawings.

This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

FIGS. 1A-4 illustrate methods of creating an embodiment of a balloon device 100 for use on a valve of a patient. FIG. 1A shows a drawing of a bulbous outer balloon 102 formed from a semi-compliant material such as Pebax, Nylon, or other materials used for angioplasty balloons. The outer balloon has two bulbs 102A, 102B and a waist 102C located between. The waist 102C preferably has a diameter 102E at a nominal pressure of approximately 2 atm between about 18-26 mm. At an inflated, zero pressure within the outer balloon 102, the waist diameter 102E is generally smaller than the 2 atm inflation size by about 1-7 mm. The bulb diameter for the bulb 102D is larger than the waist diameter 102E by 1-7 mm at the pressure of 0.1 to 2 atm.

Figure 1B:
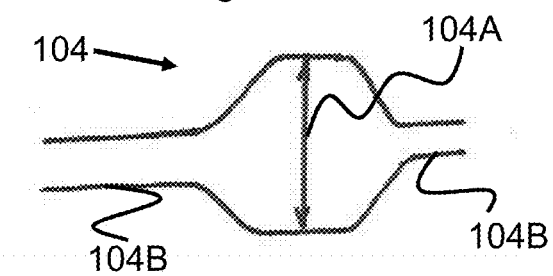

Inside of the outer balloon is located an inner balloon 104 shown in FIG. 1B. The native diameter 104A of this balloon 104 at an inflated but zero or near-zero pressure is preferably within a range of about 18-26 mm. When the inner balloon 104 is formed from a non-compliant material such as PET or a non-compliant Nylon or other material, the balloon diameter 104A inflates to a size larger than the outer balloon waist diameter 102E. The inner balloon 104 can be folded and placed within the outer balloon 102; the inner balloon distal tail 104B or tube sections are bonded to the outer balloon distal tail 102F to form a fluid tight seal between the two balloons. A guidewire-sized tubing can be place inside of the inner balloon tails 104B to form a guidewire lumen for passage 106 (FIG. 4) for a guide wire. Alternately, multi-lumen tubing can be used to provide lumens to independently inflate the outer balloon 102, the inner balloon 104, and provide passage for a guidewire. A separate lumen can also be provided to inflate the proximal and distal bulbs of the outer balloon independently if desired due to potential contact of the waist by the inner balloon causing each bulb to require a separate inflation lumen.

Figure 2:
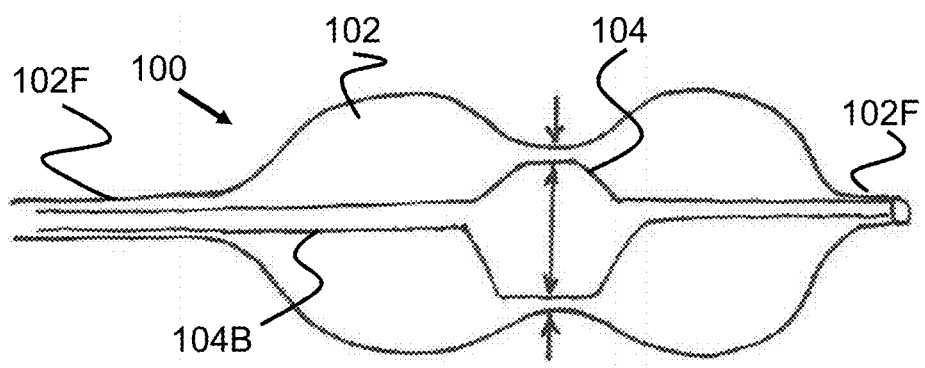
Figure 6:
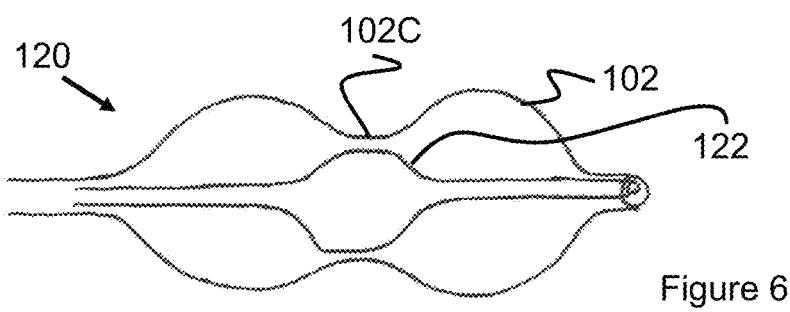
FIGS. 6-9 are various side views of a valvuloplasty balloon according to the present invention.

Upon increasing the pressure of the inner balloon 104 higher than that of the outer balloon 102, the inner balloon 104 will inflate and place the outer surface of the inner balloon 104 into contact with the waist of the outer balloon. This can occur via several different scenarios. First, for example, the outer balloon 102 (or inner and outer balloon together) can be inflated to, for example, 2 atmospheres or more to dilate leaflets of an aortic valve. Then, upon further inflation of the inner balloon 104 to a pressure of approximately 2 atm wherein the waist of the outer balloon has not yet made contact with the annulus 12 (FIG. 3). The inner balloon 104 is expanded into contact with the outer balloon waist as shown in FIG. 2. The diameter 104A of the inner balloon 104 has not reached its potential fully inflated diameter because it is being constrained by the waist 102C of the outer balloon 102. As seen in FIG. 5, the volume of the inner balloon at this time is represented by point Vm and its internal pressure, Pi, is at a magnitude of Pm. The waist diameter 102E of the outer balloon can be, for example, about 21 mm and the inner balloon diameter 104A, can also be about 21 mm at about 2 atm.

Upon further inflation of only the inner balloon 104, the pressure of the inner balloon 104, Pi, increases to a larger value, PI, as the inner balloon volume is VI. The waist 102C of the outer balloon 102 has likely made contact with the annulus 12 at this pressure. The magnitude of PI, for example, is about 2.2 atm.

If additional contrast medium is added to the inner balloon 104, its pressure, Pi will continue to grow and the inner balloon 104 can grow to its fully inflated diameter 104A, as shown in FIGS. 1B and 4. This fully inflated diameter 104A, can be equal or larger than the native inner balloon diameter (i.e., inflated to a near-zero pressure). The inner balloon 104 can grow, for example, to a diameter of 24 mm to make contact with the aortic annulus 12 having a diameter of, for example, 24 mm (FIG. 3).

The pressure versus volume curve for the inner balloon is shown in FIG. 5. As the outer surface of the inner balloon 104 makes contact with the waist 102C of the outer balloon 102, a slope change at point 110 is observed with the slope being altered to reflect the compliance of the outer balloon waist 102C. As additional volume is added to the inner balloon 104 alone, the waist 102C will grow to a diameter 102E where it makes contact with the annulus 12 of the valve. Here a large inflection point 112 is observed. At this point the physician can examine the diameter of the annulus via fluoroscopy, or other techniques to determine the diameter of the annulus. From this determined diameter, a properly sized percutaneous aortic valve implant can be identified.

Figure 7:
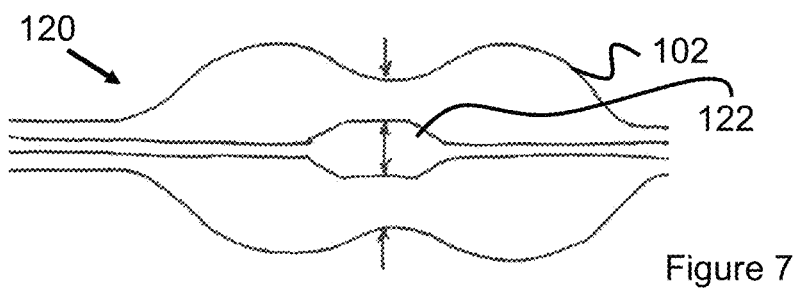

Another embodiment of a balloon device 120 is shown in FIGS. 6-9, which is generally similar to the previously described balloon device 100. However, the device 120 includes an inner balloon 122 formed from a semi-compliant material rather than a non-compliant material already discussed. For example, a semi-compliant Pebax or Nylon can be used for the inner balloon 122. The diameter 122A of the inner balloon 122 in a native state, at zero or small pressure of 0.5 atm may be similar to the diameter of the outer balloon waist 102C (FIG. 6), or it can be somewhat smaller than the waist 102C as shown in FIG. 7. The waist 102C may have an example diameter in this state between about 15-18 mm.

Figure 8:
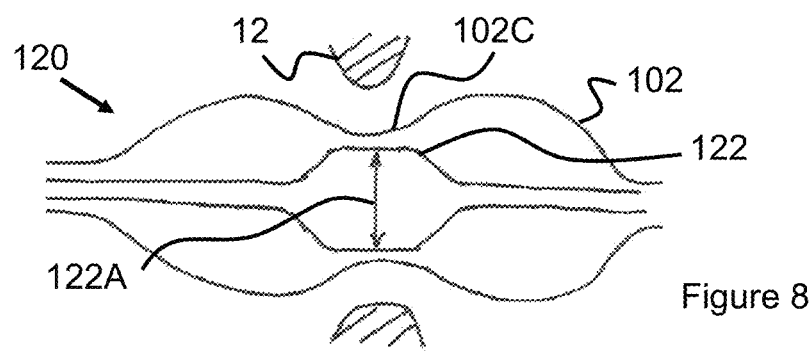
Figure 9:
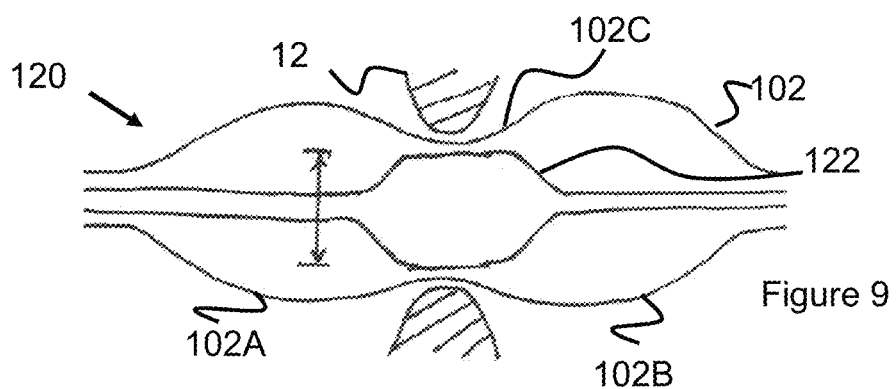
Figure 10:
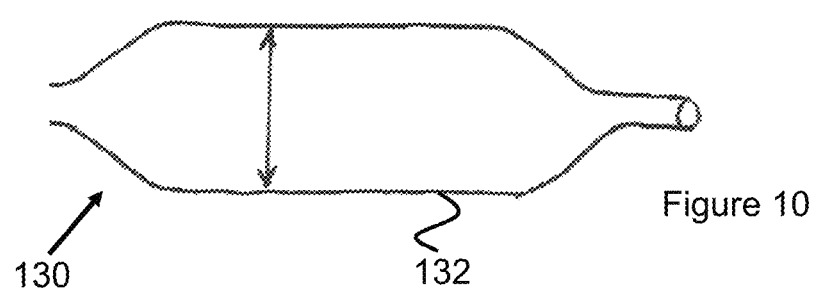

Upon expansion of the inner balloon 122 under pressure, it enlarges and comes into contact with the waist 102C of the outer balloon 102, as shown in FIG. 8. For example, both the diameter 122A of the outer surface of the inner balloon 122 and the diameter of the waist 102C could be about 18 mm. Further inflation causes the inner balloon 122 to expand outwards under pressure and the waist of the outer balloon 102C into contact with the annulus 12 as shown in FIG. 9. Such contact of the waist 102C with the annulus 12 could occur, for example, at about 24 mm in diameter. The diameter of the bulbs 102A and 102B at this inflation point could be approximately 6 mm larger, ranging from 22-30 mm.

The inflection points obtained using an inner balloon 122 that is semi-compliant are also show by the same general curves found in FIG. 5. The curves for the semi-compliant inner balloon 122 do not demonstrate as significant of a slope change as those shown for the non-compliant inner balloon. The physician would more readily observe the slope change and inflection point identified using a non-compliant inner balloon 104.

A single, bulbous balloon device 130 is also contemplated in accordance with the present invention, having non-compliant bulbs and a semi-compliant waist. Several methods are presented for constructing such a device. Turning first to FIGS. 10-14, a first a cylindrical balloon 130 can be formed from a single extrusion tubing 132 or from a coextruded tubing of two or more different materials.

Figure 11:
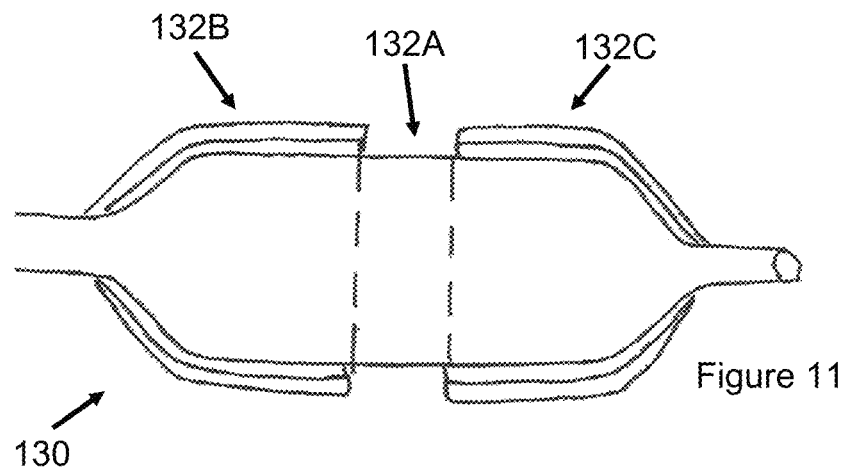

The cylindrical balloon 130 is exposed to laser ablation in the region 132A that is intended to become the waist of the final balloon. The laser ablation removes material from outer portion of the wall of the balloon 130. For a coextrusion, the laser can ablate the outer layer of material. For example, for a balloon formed from a Nylon outer layer and a Pebax inner layer, the laser can ablate the outer Nylon layer in a region of approximately 3-10 mm length in the central regions of the balloon as shown in FIG. 11. For a wall thickness that has 0.002 inches of Nylon on top of 0.002 inches of Pebax, the Nylon layer could be removed via a laser leaving the more semi-compliant Pebax remaining in the waist region. The regions 132B and 132C that are intended to become the bulbs would still contain both layers and hence would be vastly less compliant, approaching a non-compliant material. The non-compliant bulbs would have a low volume increase during pressurization and a diameter increase of less than 0.5 mm/atm during expansion of the balloon.

Figure 12:
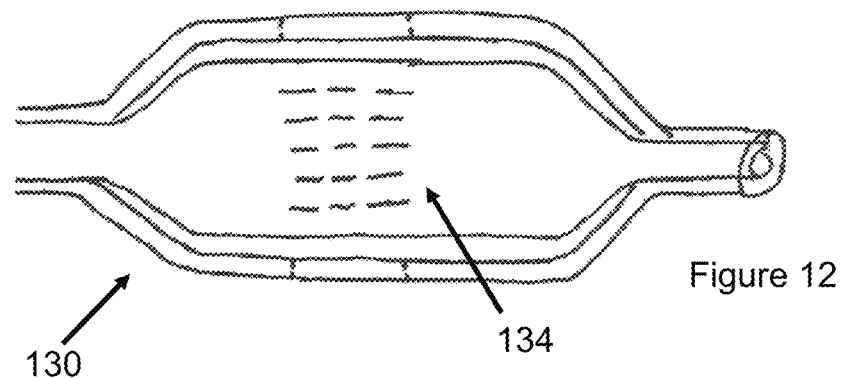

The cylindrical balloon 130 could also have axial slits 134 made along a center region of the balloon's perimeter as shown in FIG. 12. The axial slits 134 would extend a portion of the way through the wall thickness and, for example, approximately 20-100 slits could be made along the perimeter of the balloon waist region.

The cylindrical balloon that has been ablated or slit in the middle waist region could then be exposed to an additional balloon blowing step in a mold 136 to form the bulbs of the balloon as shown in FIG. 13. The bulbs 130A and 130B are blown to a desired inflation diameter 130D while the waist 130C is also blown to a desired inflation diameter 130E as shown in FIG. 14. The resulting balloon 130 then has generally non-compliant bulbs and a semi-compliant waist and can be used as described earlier to identify an inflection point in the pressure versus volume curve as the waist 130C makes contact with the valve annulus 12.

Figure 17:
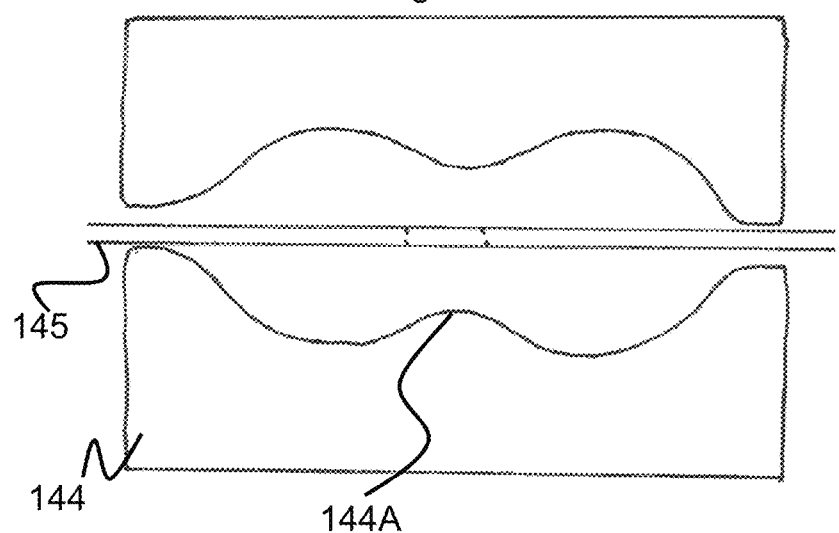
Figure 18:
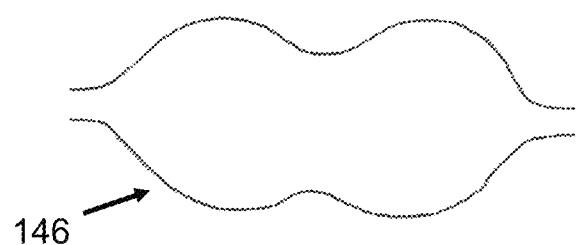

As an alternate method of forming a bulbous balloon having non-compliant bulbs and a semi-compliant waist, the tubing can be ablated prior to forming the balloon as shown in FIGS. 15-18. A single extrusion tubing, a coextruded tube, or a multi extrusion tube 140 (see FIG. 15) can be ablated via laser to form axial slits 142 through a portion of the tubing wall (FIG. 16). If the tubing 140, for example, has Nylon on its outer layer and Pebax on its inner layer, slits can be formed through the outer Nylon layer. This tubing 140 can then be placed into a bulbous mold 144 as shown in FIG. 17 with the ablated slits located adjacent the waist portion 144A of the mold 144. Upon application of pressure and increased temperature, a balloon can be formed onto a tube 145 with desired properties as described for a bulbous balloon with a semi-compliant waist and non-compliant bulbs. The extruded tubing can alternately be ablated along its entire perimeter and for a length that provides the waist of the final balloon that is formed with a bulbous region on each side of the waist.

FIGS. 19A-21 show an embodiment of a bulbous balloon 150 having a semi-compliant waist and non-compliant bulbs, the pressure versus volume compliance curve for this balloon, and a pressure control assembly. The balloon can be formed from a single semicompliant polymer such as Pebax, Nylon, or other suitable polymer with a waist that has greater compliance than the bulbs.

Figure 19A:
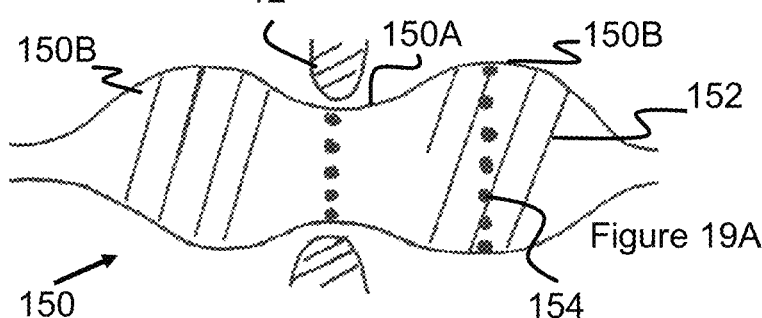

Alternately the balloon can have fibers 152 located in the bulbs 150B to restrict expansion of the bulbs 150B and forcing the waist 150A to expand upon volume injection after the bulbs 150B are fully expanded. The fibers can be formed from a braid that extends throughout the entire balloon 150 but has a lower angle of fiber with respect to the axis of the balloon 150. Alternately the fibers 152 can be wound in spirals around each of the bulbs 150B and the end cone-like regions as seen in FIG. 19A to restrict diametric expansion of the bulbs 150B.

The semi-compliant waist 150A is set in diameter such that it does not expose the annulus 12 to forces that can cause it to dissect. The semi-compliant waist 150A can be preferably somewhat smaller in diameter than the annulus 12 in its equilibrium state at pressures of 0-0.25 atm. The balloon thereby provides therapeutic benefit to the patient by expanding the valve leaflets located adjacent the bulbs 150B while protecting the annulus 12 from potential dissection due to forces imposed by the waist.

Figure 20:
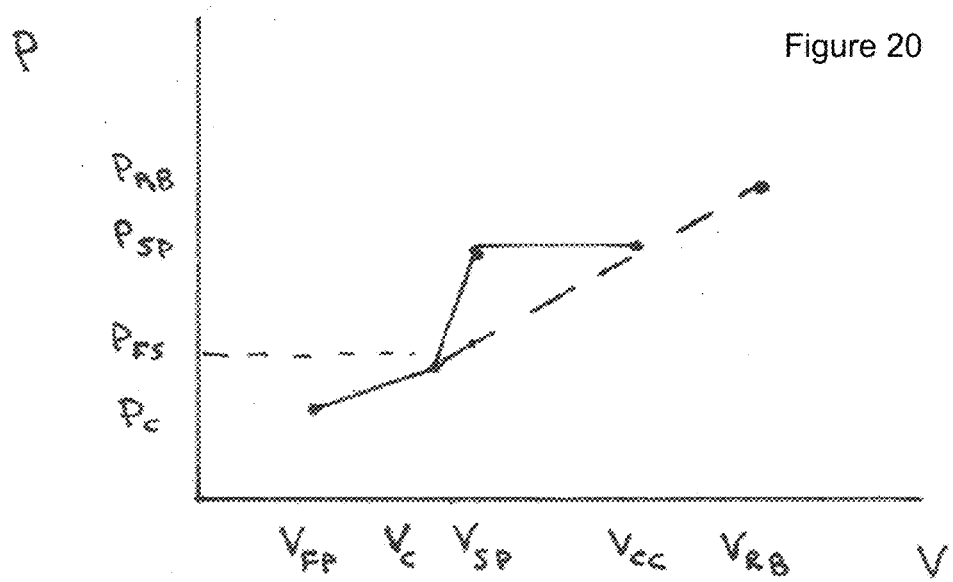
FIG. 20 is a graph showing a pressure vs. volume relationship for valvuloplasty balloons of the present invention.

Referring to FIG. 20, a volume, Vfp, of fluid is injected into the balloon 150 to cause the leaflets to fracture at a fracture pressure, Pfp (i.e., a pressure within the balloon 150). The fracture pressure may be approximately 2 atm. Following therapeutic expansion of the leaflets, the waist 150A is expanded into contact with the annulus 12 to help determine the diameter of the annulus via fluoroscopic edge to edge measurement. A volume of inflation fluid, Vc, is injected into the balloon 150 to expand the waist 150A into contact with the annulus 12 at pressure, Pc. Further expansion of the balloon waist by injection of additional fluid volume, Vsp, causes the pressure to increase at a larger post-contact slope until it reaches a set pressure or spill off pressure, Psp, above which a pressure relief valve prohibits further pressure increase within the balloon 150 and allows any further volume injected to be spilled off. This pressure relief and volume spill off ensures that excessive force cannot be applied to the annulus 12 to cause it to dissect. Normally, in free space, the volume that would be required for injection to reach the spill off pressure according to the compliance curve would be Vcc. The net spill off volume, Vns, is equal to Vcc−Vsp; this is the net volume that would be spilled off by the pressure relief valve due to contact of the balloon 150 with the annulus 12 due to injection of a volume of Vcc and contact of the waist of the balloon with the annulus and thereby restricting the volume within the balloon to contain the injected volume. As per the compliance curve, the balloon waist 152A could expand in free space to a volume of Vrb at its rated burst pressure, Prb, which can range from approximately 2.5-4 atm.

Upon observation of a net spill off volume, the operator knows that the waist 150A of the balloon has made contact with the annulus. If no spill off volume has been noted, a larger fluid volume can be injected until the waist makes contact with the annulus and a net spill off volume is measured. After contact has been confirmed due to a presence of a net spill off volume, Vns, the operator can use fluoroscopy to determine the diameter of the waist 150A using edge to edge measurement of the balloon 150 which contains contrast medium so as to be seen under fluoroscopy. To ensure that the balloon 150 is aligned perpendicular to the fluoroscopy camera, radiopaque markers 154 can be located around the perimeter of the waist 150A and/or the bulbs 150B. Observation of a line of perimeter marker dots indicates that the balloon axis is perpendicular to the camera x-ray direction; the presence of a circle indicates that the camera is directed perpendicular to the axis of the balloon 150; an oval shape indicates that the camera and balloon 150 are at an oblique angle; ie., the axis of the camera x-ray is oblique to the plane of the radiopaque marker ring.

Figure 19B:
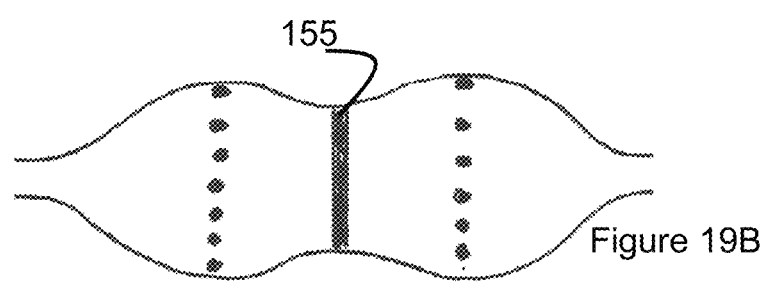

The radiopaque ring can be formed from a series of radiopaque dots 154 as shown in FIG. 19A or it can be formed from a solid ring 155 of radiopaque material deposited upon the outer surface of the balloon as shown along the balloon waist of FIG. 19B. The radiopaque material can be formed from a suspension of small radiopaque particles such as tungsten, gold, or platinum particles suspended into a polymeric material such as Pebax, Nylon, or other suitable polymer along with a suitable solvent. Such a radiopaque ring can expand in perimeter as the balloon diameter increases with increasing pressure.

Figure 21:
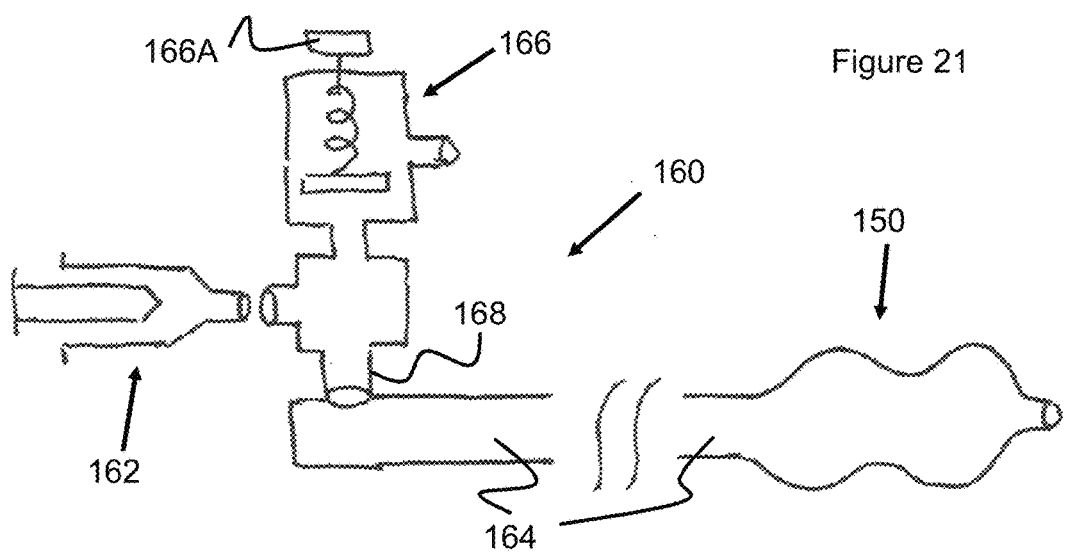
FIG. 21 is a media inflation device for inflating a balloon catheter according to the present invention.

One embodiment for the pressure relief valve 160 is shown in FIG. 21, which is part of the pressure control assembly. The pressure relief valve 160 is connected in fluid communication with an inflation device 162 such as a syringe and with the balloon inflation lumen 164 of the balloon catheter having a bulbous balloon 150 mounted at its distal end.

Upon reaching a specified spill off pressure, Psp, any further fluid injected via the syringe 162 is spilled off rather than being delivered to the balloon 150. The pressure relief valve 166 has a pressure set knob 166A that controls the pressure above which fluid inflation volume is spilled off. This pressure can be, for example, 2 atmospheres. A flow resistor 168 (e.g., a narrowed tubular passage) can be located between the inflation lumen 164 and the pressure relief valve 166 so that any pressure spike created by the syringe 162 does not result in volume spill off. Volume spill off should occur when the pressure within the balloon 150 is greater than the predetermined spill off pressure.

Bulbous balloons of the present invention that have a semi-compliant waist and non-compliant bulbs confer a safety to the patient to ensure that the annulus 12 is not exposed to pressures that may cause dissection of the annulus 12. The outward force provided by the waist of the balloon onto the annulus is less than the pressure found within the balloon. This reduced outward force is due to the restraining force acting inward toward the center of the balloon being provided by the elastic restraining force of the balloon to return to a smaller diameter. Therefore, the outward force acting by the balloon onto the annulus 12 when the balloon is at its spill off pressure, Psp, is equal to Psp minus the pressure required to place the balloon into contact with the annulus, Pc. At Pc the restraining force inward from the balloon is equal to the outward pressure acting within the balloon, Pc, which acts to hold the balloon at that diameter. Thus the net force acting outward against the annulus at the spill off pressure is Pnet outward=Psp-Pc.

Figure 22:
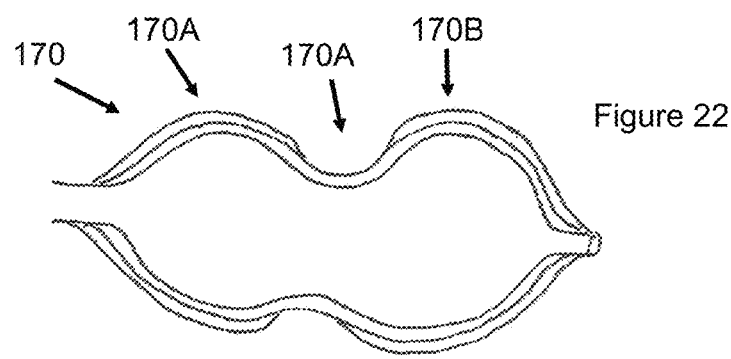
FIGS. 22 and 23 are side views of valvuloplasty balloons according to the present invention.

Many of the embodiments for the balloon presented in the present invention can be used with the pressure control assemblies presented to provide both a therapeutic dilation of valve leaflets and a diagnostic measurement of the annulus diameter. Another embodiment of a balloon 170 that can be used with the pressure control assemblies in this specification is shown in FIG. 22. This balloon 170 has a waist region 170A that is more compliant than the bulb regions; the bulb regions are preferably made to be non-compliant or only slightly compliant, e.g., less than 0.5 mm of diameter change per atmosphere of pressure for a bulb diameter ranging from 22-30 mm. This balloon 170 is formed from a coextrusion of two materials, for example, with Nylon on the outside and Pebax on the inside. Other materials can be used to for the balloon including polyethylene terephthalate, polyethylene, polyurethane, and other materials used in the formation of diagnostic and therapeutic balloons used in medical devices. Following the formation of the balloon, the outer layer or a portion of the balloon wall has been removed via a laser ablation or other means including mechanical or chemical removal. The waist region 170A can also be weakened by ebeam or other radiation techniques.

Figure 23:
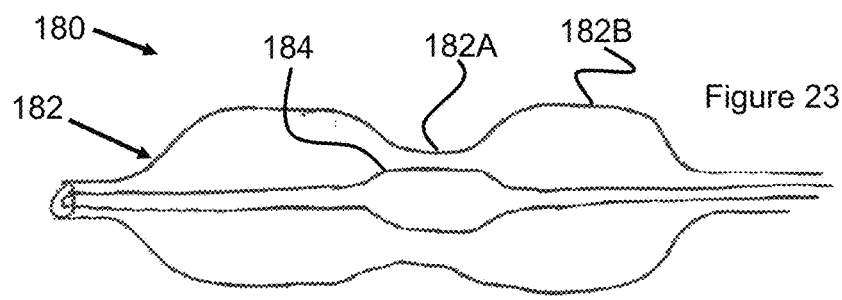

A further embodiment for the balloon that is used with any of the pressure control assemblies of the present invention to provide both therapeutic dilation of valve leaflets and diagnostic measurement of the valve annulus is shown in FIG. 23. An outer bulbous balloon 182 is formed from a semi-compliant material such as Pebax or a low durometer Nylon such that the waist is able to be smaller in diameter than the annulus 12 at approximately 2 atm when the leaflets are typically fractured and pushed aside. The waist 182A is then capable of expanding out an additional 2-4 mm in diameter as the pressure is increased to approximately 2.1-4 atm. The inner balloon 184 is smaller in length and fits within the outer balloon 182 and is located adjacent the waist 182A of the outer balloon 182. The inner balloon 182 can be either semi-compliant with a diameter that is similar to (can be slightly smaller or larger than) the diameter of the waist 182A when fully inflated. Alternately, the inner balloon 184 can be non-compliant and can have a diameter that is large enough to ensure contact with the annulus 12. Thus for an annulus diameter of 22 mm, a non-compliant inner balloon 184 could have a diameter that is 23-25 mm, for example, such that it can push the waist 182A of the outer balloon 182 into contact with the annulus 12.

The compliance curve shown in FIG. 20 is generally applicable to the embodiment shown in FIG. 23, except that the volume injected during the expansion of the waist 182A is injected into the inner balloon 184 and the pressure control assembly 160 is responsive to the pressure within the inner balloon 184. When the pressure within the inner balloon 184 reaches the contact pressure, Pc, the inner balloon has pushed the waist of the outer balloon into contact with the annulus. As a volume of media, Vcc, is injected into the inner balloon 184, is received within the inner balloon 184 without spill off of excess volume media. However, if the waist 182A of the balloon 182 makes contact with the annulus 12, the pressure will rise at a higher post-contact slope and the spill off pressure within the inner balloon 184 will be reached at a lower volume, Vsp. The net spill off volume, Vns, (Vns=Vcc−Vsp) will be spilled off and not delivered to the balloon 180. The pressure control assembly 160 of the present invention would provide a spill off of fluid volume once the spill off pressure, Psp, had been reached. Once it has been identified that a net spill off volume has been observed, then known contact has been made with the waist 182A and the annulus 12, and fluoroscopy can be used to determine the diameter of the annulus. Radiopaque markers can be placed along the perimeter of the waist 182A or bulb 182B to ensure that the balloon 182 is aligned perpendicular with the fluoroscopy camera.

Figure 24:
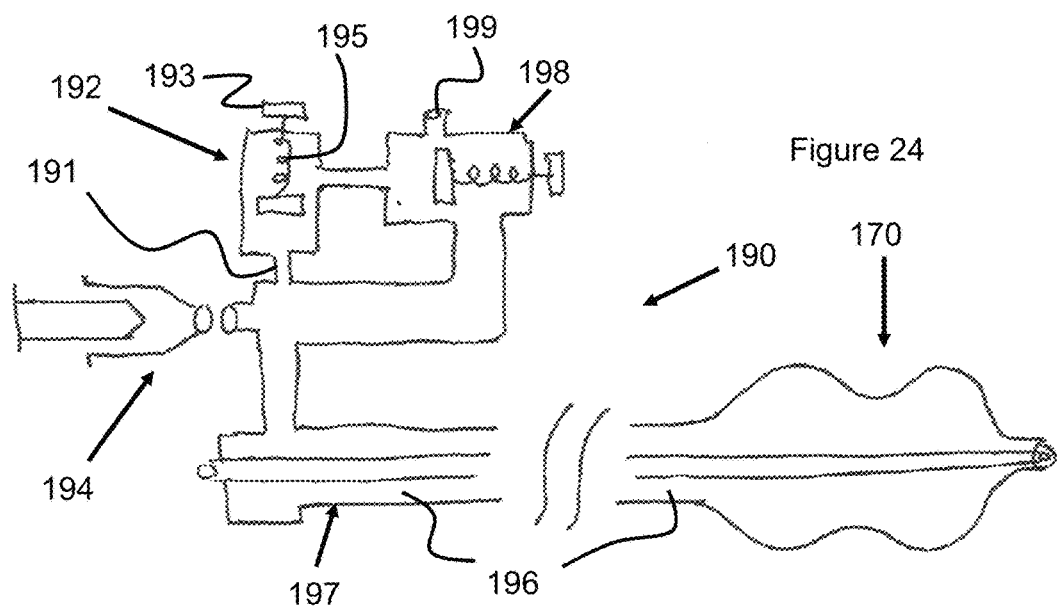
FIGS. 24-26 are media inflation devices for inflating a balloon catheter according to the present invention.
Figure 25:
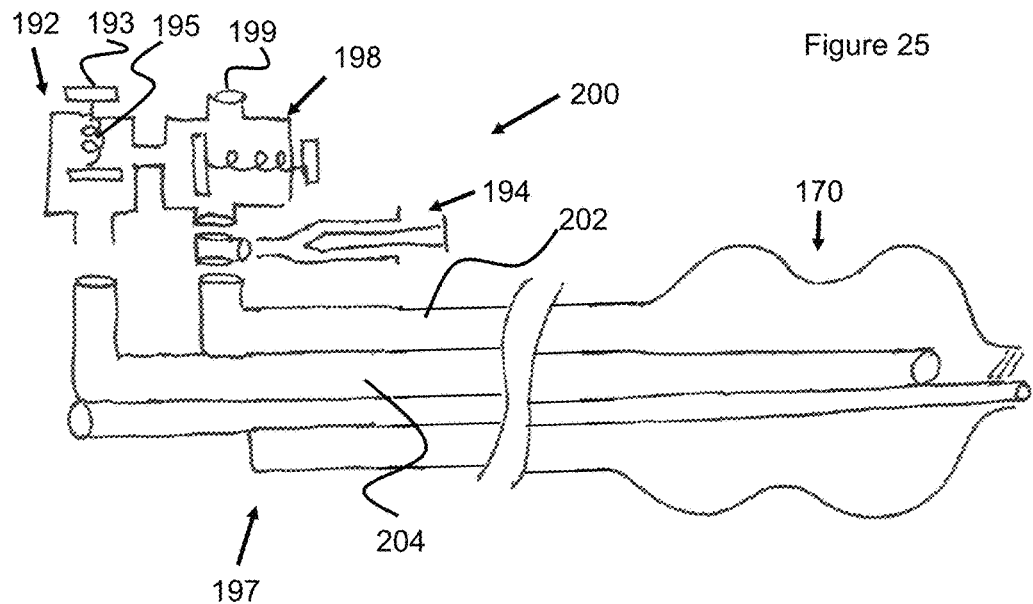
Figure 26:
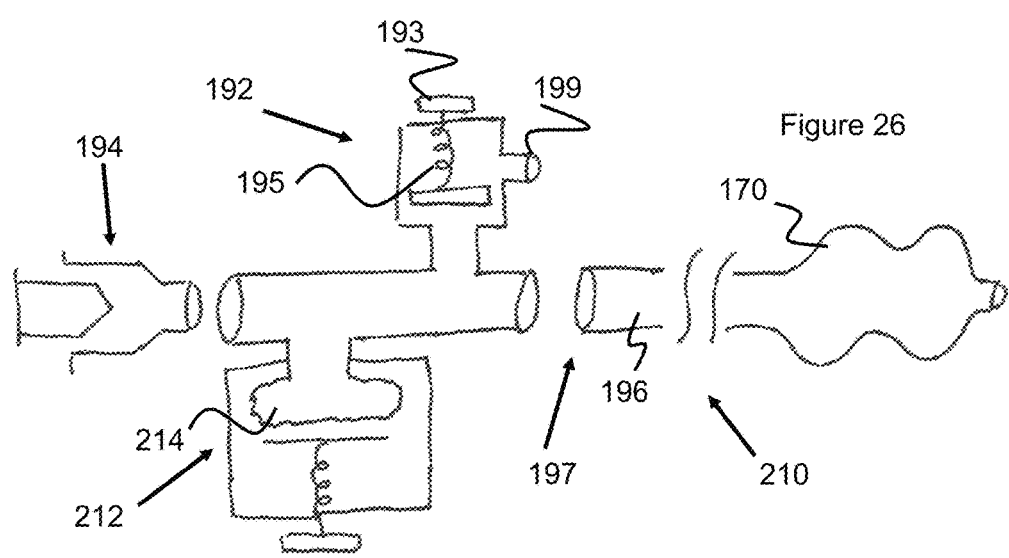

Other embodiments for the pressure control assembly (PCA) are shown in FIGS. 24-26. In one embodiment 190 shown in FIG. 24, a pressure relief valve 192 is connected to an inflation device such as a syringe 194 and also in fluid communication with the balloon inflation lumen 196 near the manifold of the catheter 197. Any spike in the pressure being injected by the syringe 194 is attenuated by a large flow resistance between the syringe 194 and the pressure relief valve 192 at bottlenecked region 191. Upon exceeding the spill off pressure as set by the pressure set knob 193 and spring 195, the pressurized media is delivered to a sliding valve 198 which is able to spill off any volume through port 199 rapidly such that a pressure spike cannot be transmitted to the balloon. Further, the spill off of volume is limited or prevented for uneven or rapid operation of the syringe 194.

Another embodiment for the pressure control assembly 200 is shown in FIG. 25. Here a first lumen 202 communicates inflation media to the interior of the balloon while a second lumen 204 is located within the catheter shaft 197, separately leading to an interior of the balloon 170. The second lumen 204 delivers fluid pressure from the balloon to the spill off valve 192. Hence, the pressure within the balloon 170 can be more accurately and evenly communicated or transmitted to the pressure relief valve 192. Inflation media is delivered to the balloon 170 via the syringe 194 and once the pressure within the balloon 170 has reached the spill off pressure, Psp, which is set by the pressure set knob 193, the primary pressure relief valve 192 is triggered to cause the secondary sliding valve 198 to spill off fluid volume from the spill off port 199. The pressure sensing lumen 202 can also be used to prep the balloon 170 at the beginning of the procedure by providing a pathway for removal of air from the balloon 170. An electronic pressure transducer placed within the balloon can also be used to monitor balloon pressure and can provide a signal to trigger the pressure relief valve 192, as opposed to the previously discussed check valve functionality.

Yet another embodiment for the pressure control assembly 210 is shown in FIG. 26. A pressure control bladder assembly 212 is located in fluid communication with the syringe 194 and the balloon inflation lumen 196 of the catheter 197. Upon exposure to a pressure spike from the inflation media, the bladder 214 is able to absorb the additional volume associated with the pressure spike and attenuate the pressure spike. A pressure relief valve 192 is also positioned in fluid communication with the balloon inflation lumen to allow relief of pressure when the spill off pressure is reached.

Figure 27:
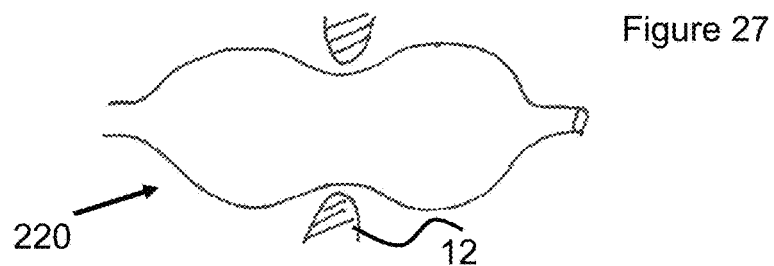
FIG. 27 is a side view of valvuloplasty balloons according to the present invention.
Figure 28:
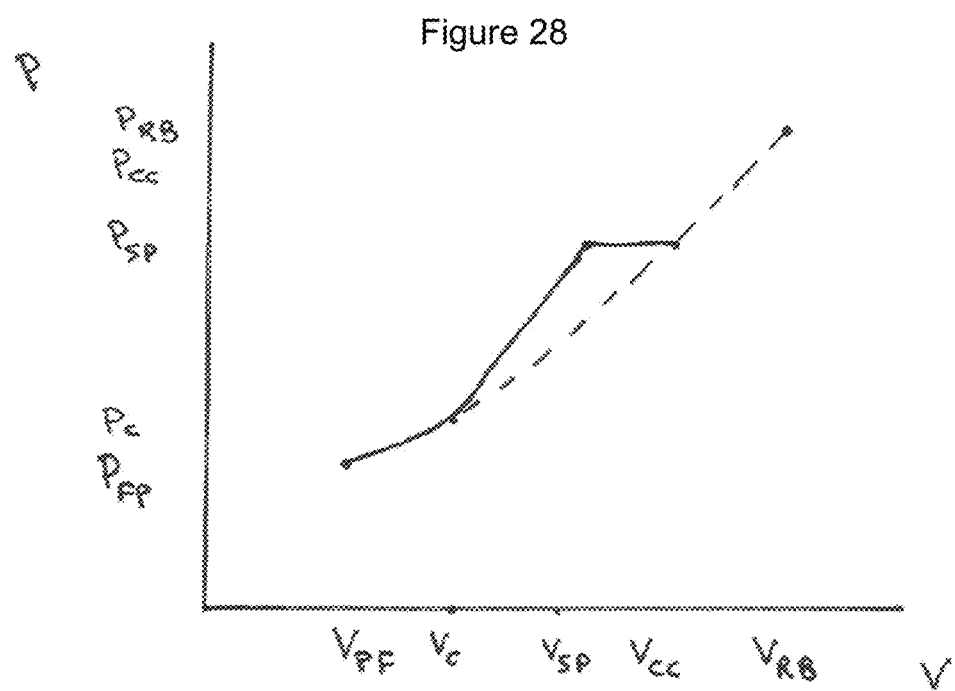
FIG. 28 is a graph showing a pressure vs. volume relationship for valvuloplasty balloons of the present invention.
Figure 29:
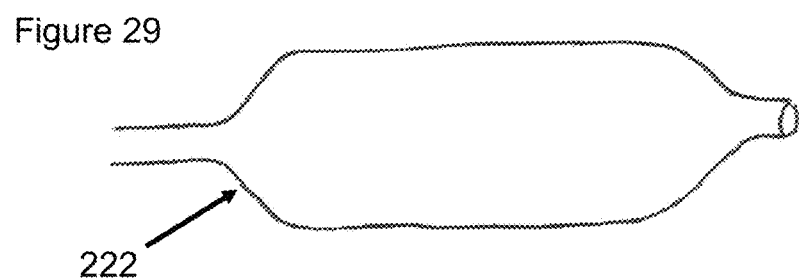
FIGS. 29-31 are side views illustrating manufacturing processes for a valvuloplasty balloon according to the present invention.

A semi-compliant bulbous balloon as shown in FIG. 27 and a semi-compliant cylindrical balloon as shown in FIG. 29 can be used along with a pressure control assembly of the present invention to measure the diameter of an annulus. The pressure versus volume compliance curve for either of these balloons is shown in FIG. 28. As Fluid is injected into the balloon the pressure rises until it reaches pressure that causes leaflet fracture, Pfp. Further inflation causes the balloon to expand such that it makes contact with the annulus at a volume inflation of Vc and pressure, Pc. Increasing the pressure above this causes the slope of the compliance curve to increase to a post-contact slope that is greater than the compliance curve slope. The spill off pressure, Psp, is set by the pressure control assembly such that all volume above the spill off volume, Vsp, is spilled off and not delivered to the balloon. If the operator injected a volume from the syringe according the compliance curve that would be received within the balloon, Vcc, there would be no spill off volume. However, if the balloon makes contact with the annulus and reaches the spill off pressure, Psp, at a volume Vsp, then the net spill off volume will be Vns=Vcc−Vsp. This net spill off volume is not as great as if the balloon had been formed with non-compliant bulbs because the post-contact slope is not as great as it would have been if the bulbs were not allowed to expand in diameter. The balloon has a compliance curve that reaches a rated burst pressure, Prb, at a specific inflation volume, Vrb.

Figure 30:
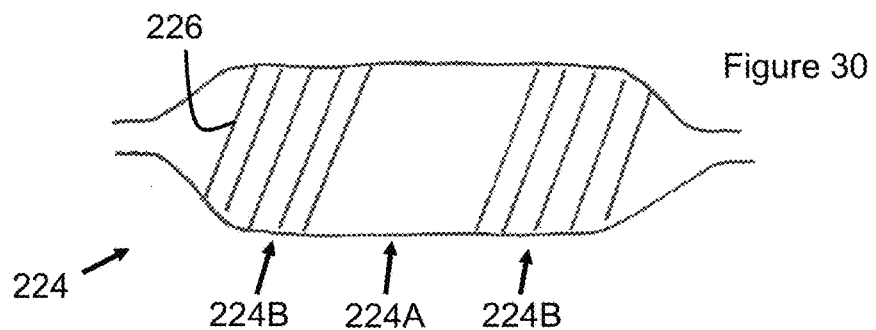

A cylindrical balloon 224 having a semi-compliant waist 224A and non-compliant end portions 224B (FIG. 30) can also be used with the pressure control assembly of the present invention to measure a diameter of a valve annulus 12. The end regions 224B can be braided or wound with fibers 226 to reduce the amount of diametric expansion as described earlier for the bulbous balloon 224. The curve that defines its compliance is similar to that described in FIG. 20. This balloon 224 would require careful positioning to locate the central portion such that it is adjacent the annulus. The bulbous balloon is automatically shaped to locate the waist 224A of the bulbous balloon so that it is adjacent the annulus.

A non-compliant bulbous balloon 228 (FIG. 31) or a non-compliant cylindrical balloon 230 (FIG. 33) can also be used with the pressure control assembly of the present invention to measure the diameter of the annulus 12. The compliance curve for either of these balloons is shown in FIG. 32. The non-compliant balloons can be formed from polyethylene terephthalate, non-compliant high durometer Nylon, or other non-compliant materials used for balloon formation in the medical device industry. These balloons would be formed such that the waist of the bulbous balloon or the diameter of the cylindrical balloon is larger than the annulus by approximately 1-4 mm. The leaflets could be dilated by another balloon prior to performing the diagnostic procedure of measuring the diameter of the annulus.

A volume, Vc, is injected into the balloon to place the balloon into contact with the annulus. Further injection of volume to the spill off volume, Vsp, causes the pressure to increase sharply at a post contact slope that is greater than that of the compliance curve to the spill off pressure, Psp. For a total volume injected by the syringe as per the compliance curve of the balloon, Vcc, a net spill off volume on Vns=Vcc−Vsp would be observed to be spilled off by the pressure control assembly.

Figure 31:
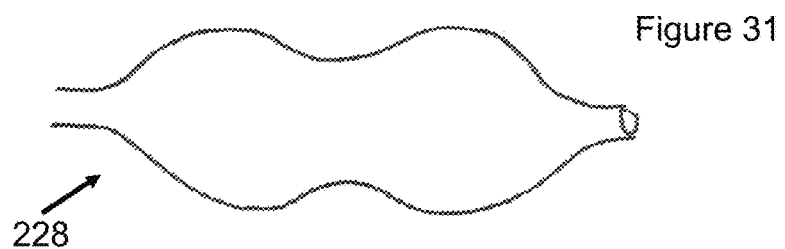
Figure 32:
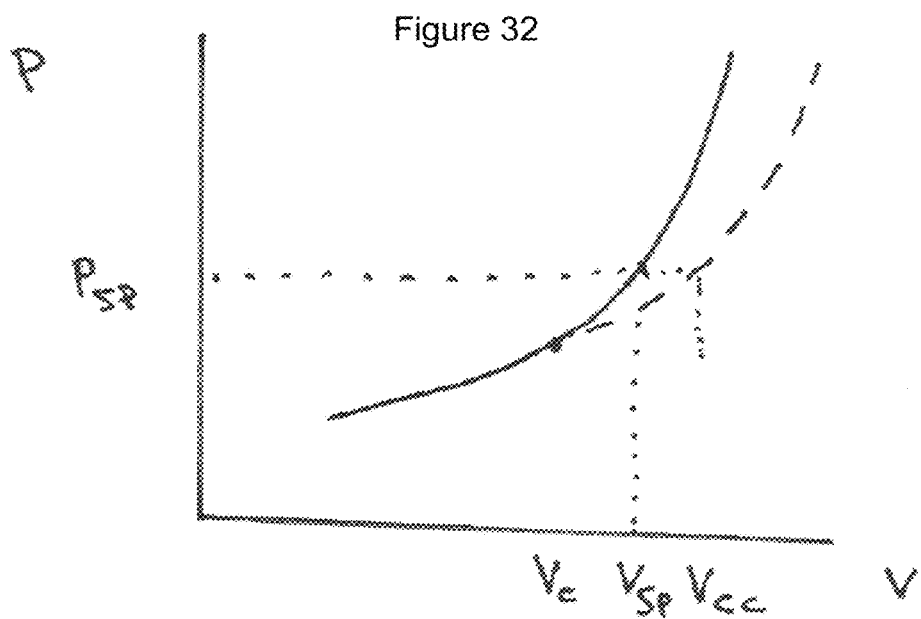
FIG. 32 is a graph showing a pressure vs. volume relationship for valvuloplasty balloons of the present invention.
Figure 35:
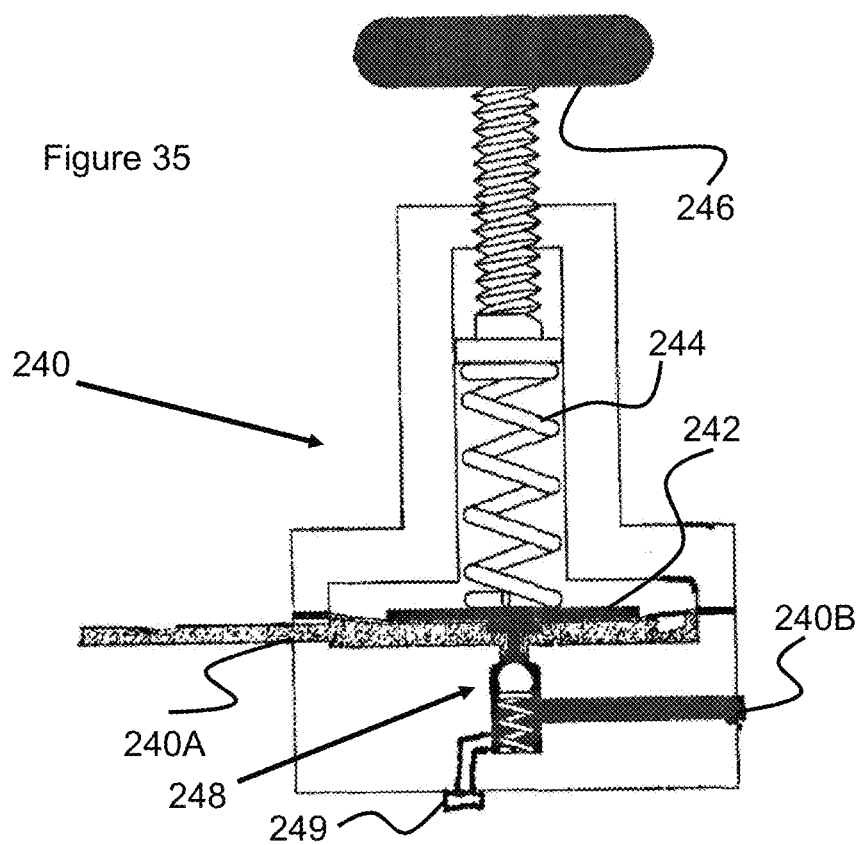

These balloon embodiments of FIGS. 31 and 33 will place the entire pressure contained within the balloon onto the annulus with potential for dissecting the annulus, thus the pressure should be maintained at a low value, less than approximately 1 atm. Since most stenotic aortic leaflets fracture at approximately 2 atm, these balloons are well suited to diagnostic measurement of the aortic diameter.

An alternate embodiment for the pressure control assembly 240 used with the catheters 197 described in this invention is shown in FIGS. 34-36B. A pressure regulator 240 is placed between the inflation device 194 and the balloon inflation port 197A of the catheter 197. The inflation device 194 is connected to the inlet port 240A of the pressure regulator 240A and the balloon inflation port is in fluid communication with the outlet port 240B of the pressure regulator 240.

The pressure regulator 240 has a diaphragm 242 that is connected via a main spring 244 to a threaded pressure set knob 246. The pressure set knob 246 is used to set the outlet pressure to a maximum pressure that is allowed to enter into the balloon 228. The diaphragm 242 controls the movement of a poppet valve 248 that restricts the flow of a high pressure flow into the inlet port 240A if the outlet pressure exceeds a specific maximum pressure. A vent 249 can be placed in communication with the fluid moving through the pressure regulator 240 and with the atmosphere outside of the pressure regulator 240 to assist in removal of air during priming of the regulator. Such a vent 249 can be found in medical devices used in the industry and often are comprised of a hydrophobic membrane that will allow air to pass through but will not allow a hydrophilic medium such as water or contrast medium to pass through.

Figure 36A:
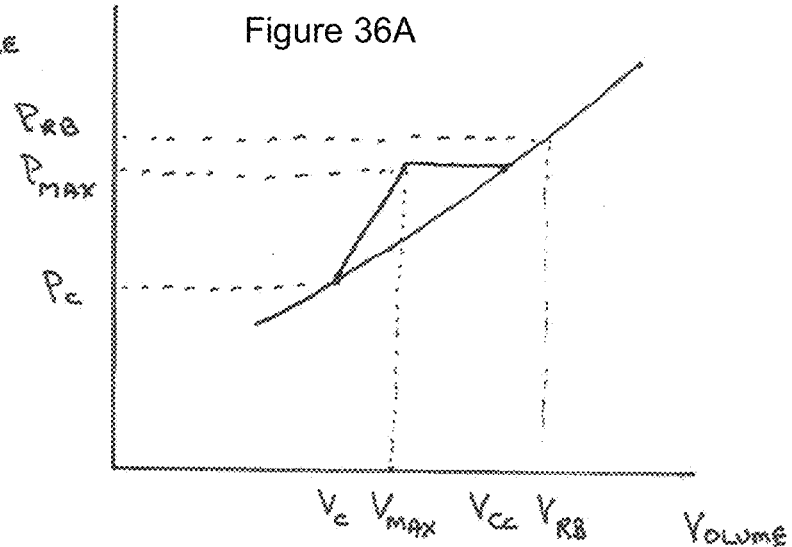
FIGS. 36A and 36B are graphs showing a pressure vs. volume relationship for valvuloplasty balloons of the present invention.
Figure 36B:
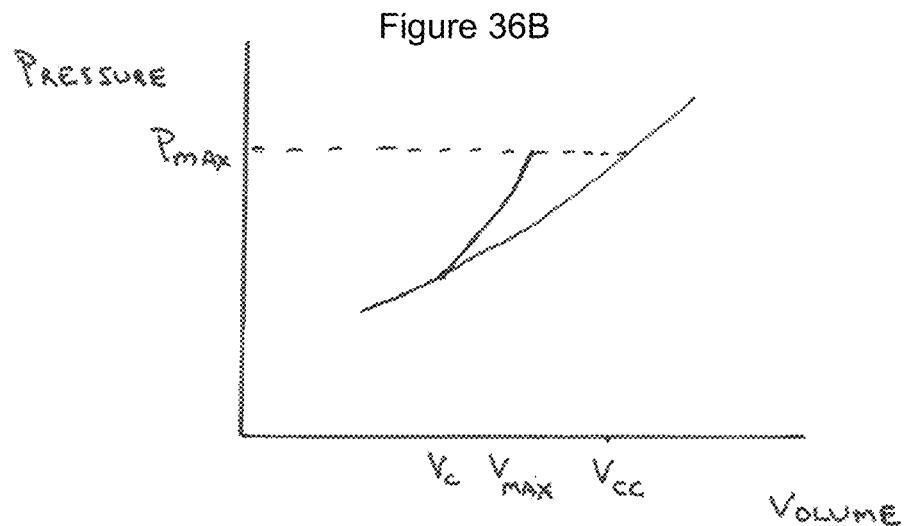

The compliance curves of FIGS. 36A and 36B reflect the pressure vs. volume relationship for the balloon in free space; the description of the compliance curve found in earlier embodiments applies to the present embodiment. A specified volume, Vcc, is placed into the syringe; this volume corresponds to the compliance curve volume that could be injected completely into the balloon to achieve a pressure, Pmax, in free space. Pmax is set at a pressure that will ensure that contact has been made between a portion of the balloon, such as the balloon waist, and the valve annulus. Pmax should not exceed a magnitude that could cause dissection of the valve annulus. Pmax can range from approximately 2.2 atm to 4 atmospheres. Typically an aortic valve annulus can withstand a pressure of 0.1-0.5 atmospheres (range 0.1-1.0 atm) without resulting in dissection. For a balloon that is formed from a semi-compliant material in contact with the waist, the pressure contained within the balloon interior is not actually applied fully to the annulus on its exterior side; instead, much of the internal balloon pressure is taken up as potential energy stored in the elastic stretch of the balloon wall; hence the internal balloon pressure is not transferred to the valve annulus. The force transferred is equal to the internal pressure within the balloon minus the pressure when the balloon first made contact with the valve annulus.

When the balloon is place adjacent to the aortic valve, however, the waist of the balloon first makes contact with the annulus at Vc and at a pressure of Pc which is below the specific maximum pressure set by the pressure regulator. The pressure within the balloon, Pc, at contact with the annulus can range from 1-2.5 atmospheres. If the waist diameter is less than the diameter observed on a pressure (or volume) versus diameter compliance curve, then the waist has made contact with the annulus and the waist diameter can be measured via fluoroscopic edge to edge to determine the diameter of the annulus.

Upon further injection of fluid from the syringe, the pressure rises to Pmax and a volume of Vmax has been injected into the balloon. The pressure regulator prohibit any further flow of fluid into the balloon as the poppet valve shuts down the inlet flow. The volume remaining in the syringe is Vnet=Vcc−Vmax as depicted in FIG. 36A for a balloon having non-compliant bulb or end regions and a semi-compliant waist or center region. The rise in pressure can be very rapid with an increased slope that is greater than the slope of the compliance curve. For a balloon formed entirely of a semi-compliant material such a Pebax, for example, the post-contact slope shown in FIG. 36B is not as great as shown in FIG. 36A however one is able to observe a volume Vnet=Vcc−Vmax that remains in the syringe after injecting into the balloon at Pmax. This net volume, Vnet, remaining in the syringe can be larger for the entirely semi-compliant balloon than the balloon with non-compliant bulbs or ends since the end regions of the semi-compliant balloon will increase in diameter and volume as the balloon internal pressure is increased. The presence of this volume, Vnet, in the syringe indicates that contact has been made between the balloon waist and the valve annulus; observation of the edge to edge diameter of the balloon under fluoroscopy is then used to determine the diameter of the annulus. Any spikes in pressure produced by excessive movement of the syringe will be stopped by the pressure regulator and not allowed delivery into the balloon.

The present pressure control assembly can be used with a semi-compliant balloon having a bulbous shape as described earlier in this invention. Even though the bulbs can expand under increasing pressures, the P vs. V compliance curve for the balloon can determine the amount of volume to place into the syringe, Vcc, and thereby be used to determine contact of the balloon with and external structure such as a valve annulus.

The bulbous balloon of the present invention can have a waist that is semi-compliant and bulbs that are non-compliant. The pressure vs. volume compliance curve will show a greater chance in slope upon contact of the waist with the annulus, but the volume left in the syringe would be less than that found with a bulbous balloon made entirely out of a semi-compliant material due to the diametric expansion of the bulbs under increasing pressure.

The present methods can also be used with cylindrical balloons that are either semi-compliant or non-compliant, or with a bulbous balloon that is entirely non-compliant with the restrictions that are the same as that described in the earlier embodiments.

Figure 37:
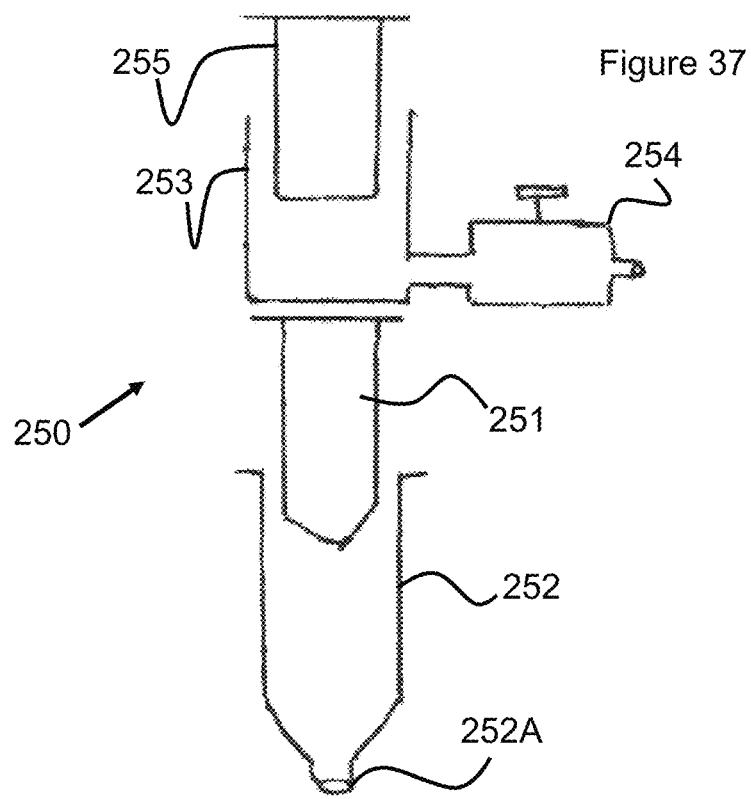
FIG. 37 is a media inflation device for inflating a balloon catheter according to the present invention.

A further embodiment for the pressure control assembly 250 is shown in FIG. 37. The inflation device 250 includes a main plunger 251 that moves within a main barrel 252. The main barrel 252 is placed into fluid communication with the balloon inflation lumen of the catheter via barrel port 252A. A specified volume, Vcc, of inflation fluid is placed into the main barrel 252. A secondary barrel 253 of the pressure control assembly 250 is located on top of the main plunger 251 and is similarly in communication with the inflation lumen of the catheter. The secondary barrel 253 is in fluid communication with a pressure relief valve 254 that provides a spill off of the secondary fluid at a set maximum pressure, Pmax. Upon advancement of the secondary plunger 255, only a specified maximum pressure, Pmax, can be delivered from the main barrel to the inflation port of the balloon catheter. As describe earlier, any inflation fluid remaining within the main barrel is an indication that contact has been made between the waist of the balloon and the valve annulus, and determination of the annulus diameter can be made using fluoroscopy.

The inflation device of the present invention can comprise a syringe that has as generally smaller diameter than other syringes found in the industry for the volume needed to inflate a typical valvuloplasty balloon (approximately 25-40 ml). Since the balloon needs to be inflated and deflated rapidly (typically within approximately 10 seconds), it is necessary to make the syringe with a direct force application that is similar to that found with a typical syringe. Ergonomic features can be added to the plunger of the syringe and to the barrel of the syringe to make the force easier to apply. Such features can be in the form of rings with larger surface area or surfaces that are easy to apply pressure against. The diameter of the syringe should be smaller such that a force of approximately 20 lbs. or less is required to generate a pressure of approximately 3 atm as a Pmax. The diameter for such a syringe should be approximately 1.6-2.2 cm to provide a comfortable application of 3 atmospheres of pressure. The travel of the syringe plunger, however can be rather large ranging from 4 to more than 5 inches.

Alternately, a cam actuated syringe is contemplated in the present invention wherein the cam requires a higher force at a smaller lever arm be applied by the operator at the initiation of filling, when the balloon is easily filled; then when the pressure in the balloon begins to increase above approximately 0.5-1 atm, the cam provides a greater lever arm to assist the operator to fill the balloon easily and rapidly with less force required by the operator. The diameter of the barrel of the syringe could thereby be enlarged to a diameter greater than 2 cm such that the travel of the syringe plunger is not as long in order to deliver the required volume of fluid to the balloon. It is anticipated that a pistol grip design and cam similar to that described in the referenced and incorporated patent, U.S. Pat. No. 7,951,111 can be used to deliver inflation fluid to the catheter. The elements shown in the above referenced patent that show a secondary floating plunger element and means to identify the location of the plunger with respect to the barrel would not be required for the present invention. A vent can be place on the inflation device if desired to help provide for removal of air contained within the inflation device. A hydrophobic membrane that allow removal of air but does not allow passage of hydrophilic medium such as contrast medium can be placed into fluid communication of the fluid contained within the barrel of the inflation device.

Figure 38A:
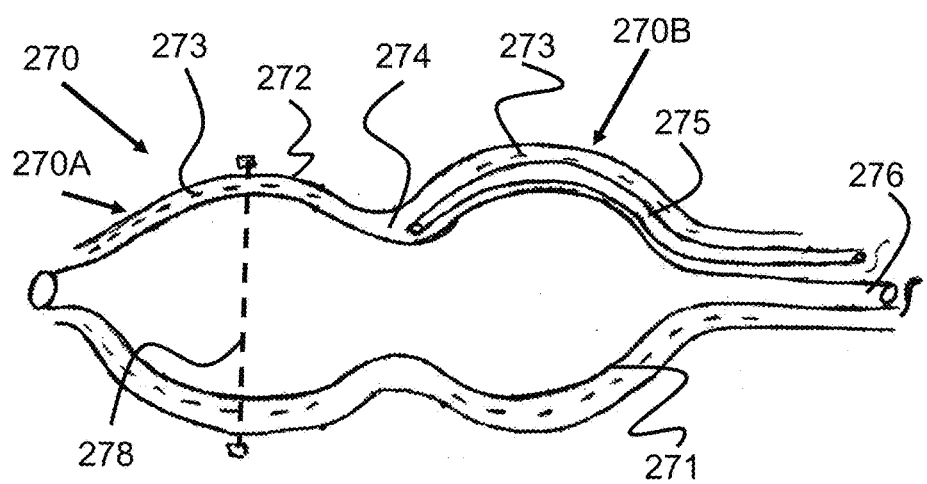
Figure 38B:
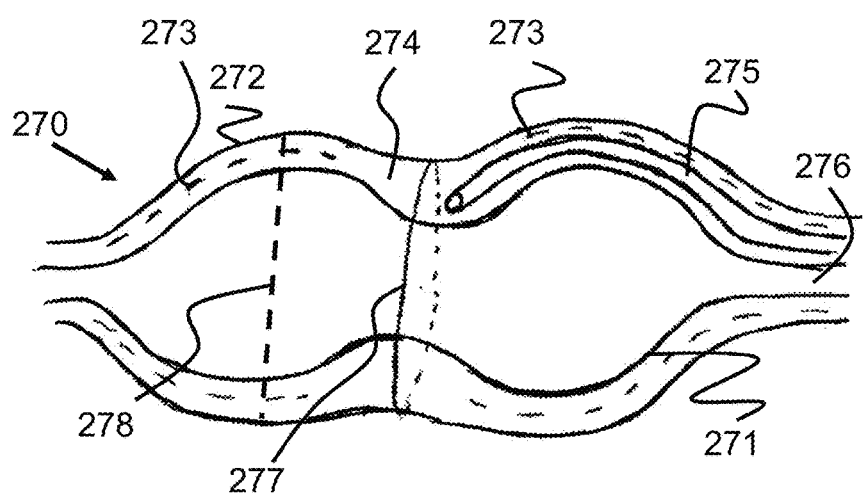

FIGS. 38A and 38B show an embodiment of a bulbous balloon assembly 270 for providing a therapeutic dilation of stenotic aortic valve leaflets followed by a diagnostic measurement of the diameter of the annulus 12. In this embodiment, an inner balloon 271 is formed from Nylon, Pebax, PET, composite, or other semi-compliant or non-compliant material suitable for dilating aortic valve leaflets and maintaining diametric dimensions of the bulb within approximately 2 mm or less at pressures ranging from 2-3 atm. The waist of this inner balloon 271 is, for example, not able to expand to meet the wide range of annular diameters that are associated with a particular aortic sinus diameter and provide a low outward force onto the annulus, independent of the diameter of the annulus. The annulus diameter is estimated by the physician using TTE, MSCT, or TEE, prior to the procedure and can easily be off by 2-3 mm or more. An outer balloon 272 formed from a compliant or softer semi-compliant polymer such as a low durometer Pebax, Nylon, silicone, latex, or polyurethane is located over the inner balloon 271 and allows the waist region of the outer balloon 272 to expand by 3 or more mm when exposed to a pressure that is low, approx. 0.5 to 1 atm (range 0.1-1.5 atm), and is lower than that required to cause an annular dissection of an aortic annulus. Less than one atm of stress can be applied to the annulus 12 to ensure that it does not dissect. The expansion of this softer waist is ensured to be large enough in diameter such that it will definitely make contact with the annulus 12 due to growth of 3-6 mm for pressure increase from 0.5 to 1 atm.

As shown in FIG. 38A the proximal and distal bulbs of the inner layer 271 and the outer layer 272 are attached together by a tie layer, forming a middle, unbonded, waist region, or waist bladder 274. The tie layer or bonded regions can be formed by dipping the inner balloon 271 into a polymeric tie layer that will melt at a low temperature, placing the outer layer 272 over the tie layers, and allowing the two layers to bond together via thermal bonding. Other tie layer applications can be used, including masking regions that are not intended to be bonded, or providing a tie layer as part of an extrusion process. A waist portion of an outer balloon can be formed and bonded at each of its ends to the inner balloon without having any bulbous portions to the outer balloon. The proximal and distal open ends of the outer waist could be bonded to the proximal and distal bulbs of the inner balloon to form a waist bladder having an unattached inner and outer waist. Bonding techniques include thermal bonding, solvent bonding, or use of adhesives.

An inflation tube or channel 275 is made or placed along the outside of the inner balloon 271 or between the inner and outer balloon in the proximal bulb to allow the waist bladder 274 to be inflated independently from the inner balloon 271. The inner balloon 271 is inflated using a separate inner inflation lumen 276. An inflation channel 275 can be formed by making an area between the inner and outer balloons such that a channel about 1-5 mm wide does not contain a tie layer. A porous material (e.g., sponge-like material) can be placed within the channel to ensure that the channel does not collapse during application of vacuum for deflation of the waist bladder.

As shown in FIG. 38B, the waist bladder 274 can be inflated after or during inflation of the inner balloon 271 which has been inflated to dilate the leaflets. The waist bladder 274 can be inflated at low pressure, such as 0.5 to 1 atm (range 0.1-1.5 atm), to cause the waist bladder 271 to expand radially outwards away from the inner layer 271, forming a diameter that is 3-6 mm larger than the middle portion of the inner layer 271. The waist bladder 271 may then make direct contact with the annulus 12.

Observation of the diameter of the outer waist or waist bladder can be made using fluoroscopy. Alternately, a radiopaque waist marker band can be placed along the perimeter of the smallest diameter nadir or central axial position along the waist to help visualization under fluoroscopy and also be used to help ensure that the fluoroscopy camera is oriented properly with respect to the balloon axis and hence the axis of the aortic annulus. The positioning of the waist of the inner balloon 271 adjacent the native aortic annulus ensures that the waist marker band 277 is located adjacent the annulus 12 and is representative of the diameter of the annulus 12. The axial position of the annulus along the tubular left ventricle outflow tract of the body is also identified and determined by the position of the marker band located adjacent the aortic annulus.

A radiopaque bulb marker band can also be located on one or more of the bulbs of the present invention. The distal bulb 270A along with a distal bulb marker band 278 located in the left ventricle outflow tract remains round in cross section when the inner balloon 271 is inflated to its working pressure of approximately 2 atm. Examination of the distal bulb marker band 278 via an oblique view presents as an oval shape with a bulb ratio of major and minor axis. Similar examination of the waist marker band under the same oblique view should reveal a similar waist ratio for its major and minor axis if the waist is indeed round in cross section. The division product of the waist ratio to the bulb ratio reveals or determines the amount of ovality found in the waist and hence reflects the ovality of the aortic annulus.

The present invention allows the inner balloon 271 to be inflated at a pressure of approximately 2 atm (range 1.5-3.5 atm) to dilate the stenotic aortic valve leaflets; the waist of the inner balloon 271 positions the balloon across the aortic annulus 12 in a way that avoids excessive contact with the annulus 12 and inadvertant rupture or dissection of the aortic annulus. The waist bladder 274 can be inflated to a lower pressure of 0.5-1.0 atm (range 0.1-1.5 atm) and make contact of the outer waist with the aortic annulus in a controlled manner without causing annular rupture. Definite contact of the outer waist of the outer layer 272 with the annulus 12 allows measurement of the diameter of the annulus. Such diameter measurement can be made under fluoroscopy or ultrasound using edge to edge measurements of the balloon filled with contrast medium or via visualization of the waist marker ring with the balloon filled with saline or a lower concentration of contrast medium.

Another embodiment of the bulbous balloon 280 with a waist bladder 274 is shown in FIGS. 39A-39D and is generally similar to previously described balloon 270. In this embodiment, a channel 282 (or more than one channel) is formed between the inner balloon 271 and outer balloon 272 where the balloons are not bonded together for a width of approximately 1-5 mm and extending from the waist bladder 274 to the distal evacuation opening 275A. The channel 282 can be formed by masking the inner balloon 271 such that a tie layer 273 is located everywhere along the outer surface of the inner balloon 271 except for the area of one or more channels 282. The waist bladder 274 or enlargement space is similarly formed by masking the inner waist or via other means such that the inner and outer balloon waists are not bonded in this the waist bladder region 274. Alternately, the waist portion of an outer balloon 272 can be bonded via thermal or adhesive means to the waist portion of the inner balloon 271 to form a waist bladder 274.

Figure 39A:
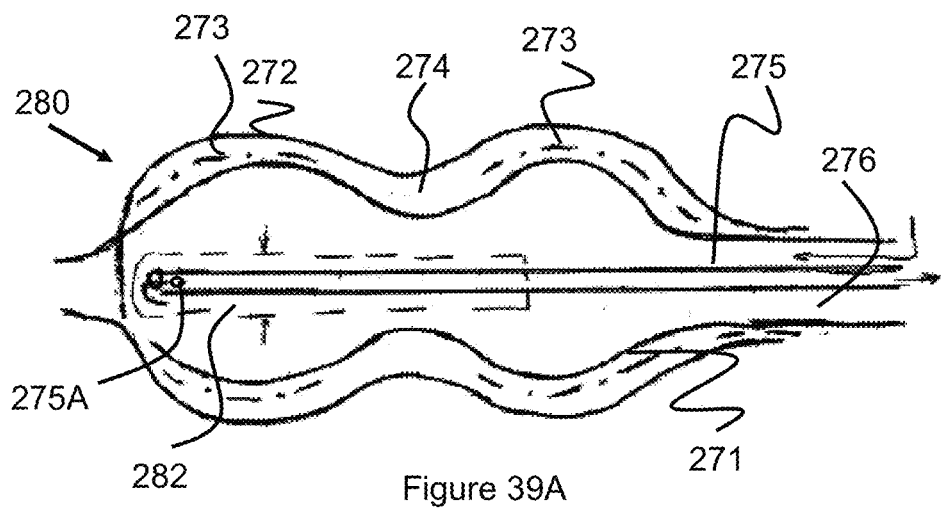
Figure 39B:
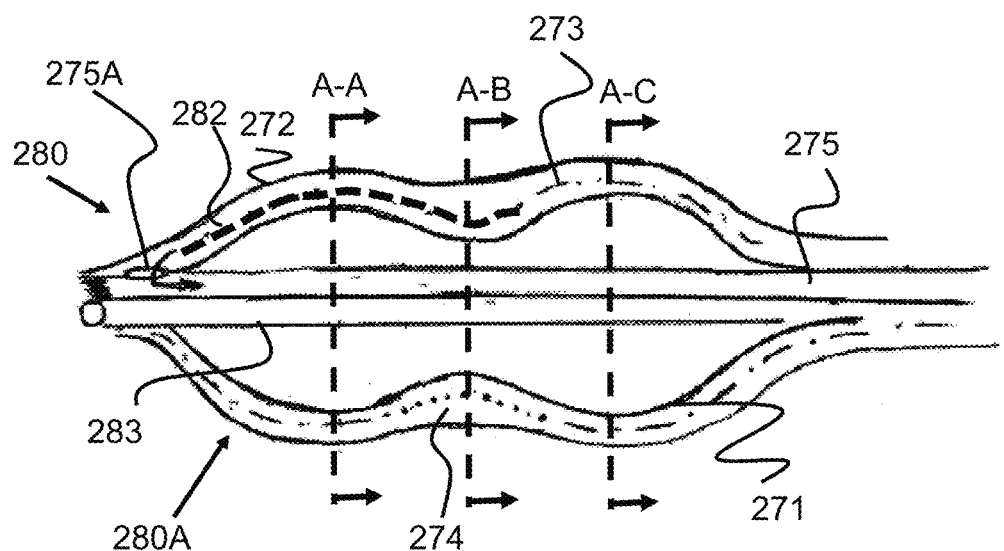

As shown in FIG. 39A the inner balloon 271 has been inflated and the outer balloon 272 has remained in contact with it to form its bulbous shape to dilate the stenotic aortic valve leaflets. The channel 282 that connects the waist bladder 274 to the outer inflation/deflation lumen 275 is facing the observer. In FIG. 39B, the catheter of FIG. 39A has been turned 90 degrees such that the channel 275 is facing upwards and the waist bladder 274 or expansion space has been filled with contrast medium causing the outer waist to expand outwards to a larger diameter. This waist bladder expansion occurs at a pressure that is low, approximately 0.5 to 1 atm (range 0.1-1.5 atm), such that the annulus 12 is not placed under excessive stress that could cause it to dissect (i.e., less than 1 atm of stress). The outer waist also expands for a significant amount such that it is ensured contact with the annulus 12. In FIGS. 39B and 39C, one can see the channel that does not contain a tie layer 273 in a portion of the distal bulb region 280A, but other parts of the distal bulb 280A are bonded together. Hence, fluid passes between the waist bladder 274, the channel 282, the distal evacuation opening 275A, and the inflation/deflation lumen 275. As shown in FIG. 39E, tie layer 273 is located everywhere else between the inner and outer proximal bulbs. As shown in FIG. 39D no tie layer 273 is located between the inner waist and outer waist in the waist 274 or waist bladder region or enlargement space.

One or more channels 282 could be placed in the proximal bulb region if desired and extended into the bladder waist 274. The channel in this case would be directly attached to a separate inflation lumen located in the catheter shaft. Care must be given to ensure that fluid used to inflate the waist bladder is not trapped due to channel collapse under vacuum when trying to evacuate the inflation fluid from the waist bladder when the inner balloon is deflated. A screen or fibrous material can be placed into the channel, for example, to ensure that such a channel is not able to collapse under application of a vacuum for evacuation of fluid from the waist bladder.

Figure 40C:
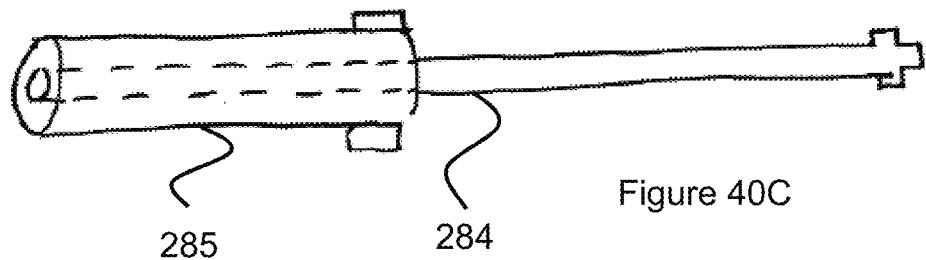

Removal of inflation fluid from the waist bladder 274 as seen in FIGS. 39A-39D is shown in FIGS. 40A-C. The inner balloon 271 can be deflated using the inner inflation lumen 275 via application of a vacuum. Blood flow through the aorta will not be significantly impeded by the small amount of fluid contained within the waist bladder 274. The balloon 280 can be withdrawn through the introducer sheath 285 as shown in FIG. 40A. When the waist 274 comes into contact with the sheath 285 as shown in FIG. 40B, the fluid contained in the waist bladder region 274 is forced distally toward the distal evacuation opening 275A and out of the evacuation lumen 275 for removal out of the manifold. The fluid contained within the bladder waist 274 is further removed as shown in FIG. 40C allowing the balloon 280 and catheter 284 to be withdrawn from the introducer sheath 285.

Figure 41:
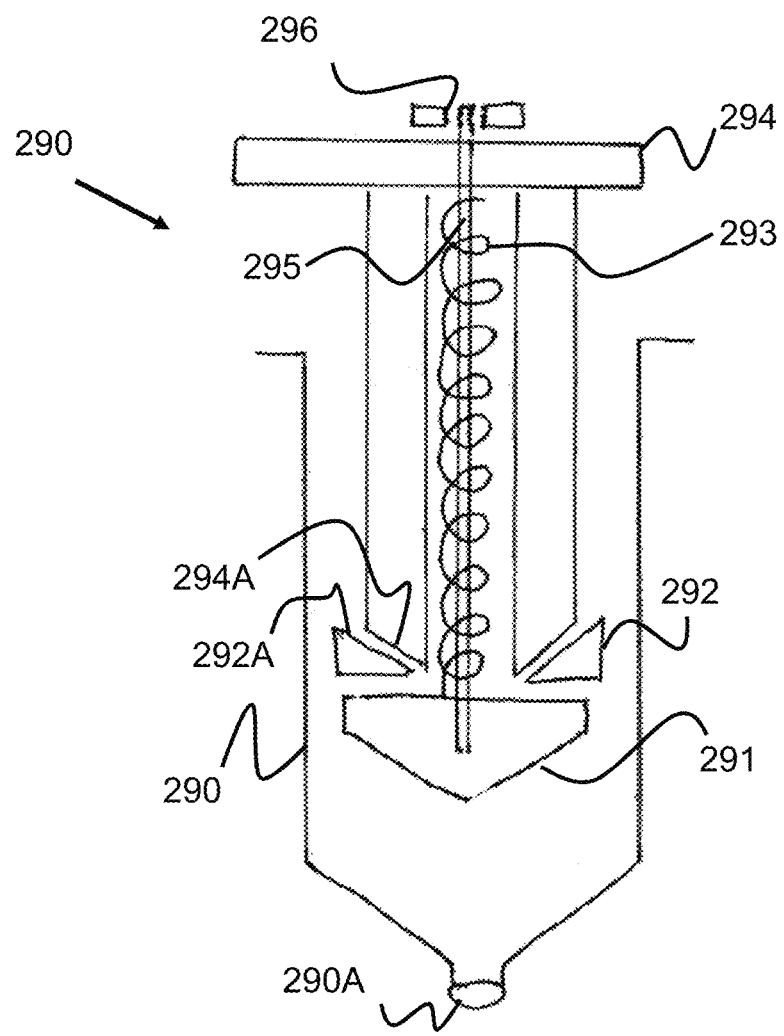
FIG. 41 is a media inflation device for inflating a balloon catheter according to the present invention.

FIG. 41 shows an embodiment for a pressure control assembly 290 of the present invention that functions similar to a syringe. Specifically, the plunger 294 is attached to the plunger tip 291 via a spring 293 or similar compressible member. The compression or tension of the spring 293 can be adjusted via a compression member 295, which is connected to a top of the plunger 294 and the plunger tip 291. The compression member 295 can be a flexible fiber, for example, that maintains the spring 293 under various levels of compression. Alternate compression members can be used to hold the spring 293 under compression while allowing the spring 293 to undergo further compression. The plunger 294 is in contact with a friction element that can move to make frictional contact with the barrel or a portion of the barrel or other member that is stationary with respect to the barrel. The spring compression can be adjusted by a compression adjustment means such as a screw that applies tension to the compression member.

As the fluid between the barrel 290 and the plunger tip 291 attains a pressure in excess of that set by the compression adjustment means 296, lower, angled surfaces 294A of the plunger 294 begin to press against upper angled surfaces 191A of the friction elements 292. The surfaces 294A and 292A are angled such that the friction elements 292 are pushed radially outward into contact with the wall of the barrel 290 thereby preventing further movement of the plunger tip 291 downward toward the barrel exit 290A. Hence, the more compressed the spring 293 is by the compression member 295, the less pressure that will be required to engage the friction members 292 and reduce or prevent further movement of the plunger tip 291. In one example, the friction members 292 can be set to engage the barrel walls at about 203 atmospheres of pressure.

Figure 42A:
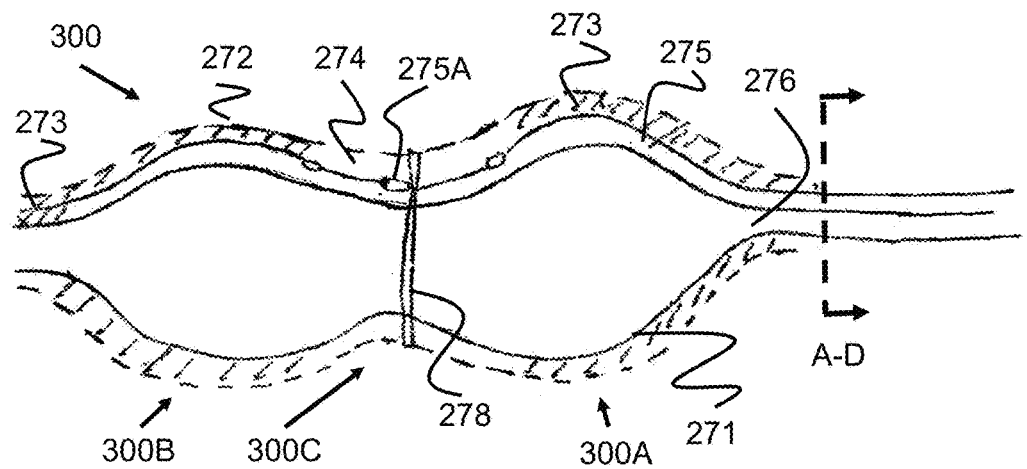
FIGS. 42A, 42B, 43A, 43B, 43C, 44A, and 44B are side views of valvuloplasty balloons according to the present invention; and, FIGS. 45A, 45B, 45C, and 46 are various views of media inflation devices for inflating a balloon catheter according to the present invention.
Figure 42B:
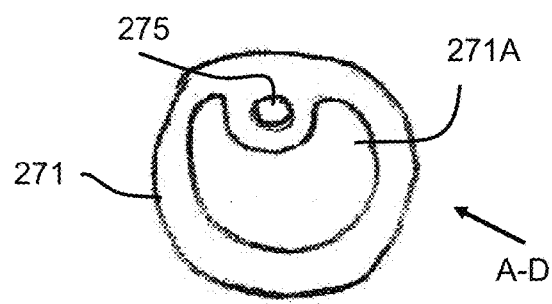

An alternate embodiment for the bulbous balloon assembly 300 having a waist bladder is shown in FIGS. 42A-42C. This embodiment is generally similar to that described earlier in FIGS. 38A-38B, but includes alternate methods of construction. This bulbous balloon 300 includes a proximal bulb 300A, a distal bulb 300B, and a central waist 300C that is of a smaller diameter than either of the bulbs at a low inflation pressure. In this embodiment an inner balloon 271 is formed from an extrusion having two lumens (see FIG. 42B), an outer inflation lumen 275 to inflate an outer balloon 272 and waist bladder 274, and an inner inflation lumen 271A that forms the main lumen of the inner balloon 271. The extrusion can be formed with more than one outer inflation lumen. For example, the extrusion could have two or more outer inflation lumens or outer lumens that can be used for either inflation or evacuation of the waist bladder 274. A tri-lumen tubing could provide, for example, an outer inflation lumen and an outer evacuation lumen for the waist bladder 274 in addition to providing an inner inflation lumen 271A for the inner balloon 271.

The duel lumen tubing is formed into a bulbous balloon using balloon blowing processing methods. The material for the inner balloon can be Pebax, Nylon, PET, a coextrusion, a copolymer, or other semi-compliant or noncompliant balloon material including composite structures containing fibers. The outer inflation lumen 275 can extend along one side of the balloon 300 throughout the entire length of the balloon 300, but at least extends through the length of the waist. One or more openings 275A are made into the outer inflation lumen 275 along the length of the waist 274. A tie layer 273 consisting of a low melting temperature polymer is coated on each of the bulbs leaving the waist region non-coated. The waist of the inner balloon 271 can be masked or otherwise processed to allow the tie layer 273 to be deposited or coated onto the bulbs alone. Other bonding methods such as thermal bonding, solvent bonding, or use of adhesives can be used to bond each end of the outer waist to the proximal and distal bulbs of the inner balloon and leaving the inner waist not bonded to the outer waist.

A softer semi-compliant or compliant outer balloon 272 is formed as a separate step and placed over the inner balloon. Alternately, a coating process can be used to form an outer balloon 272 over the inner balloon 271 using spray coating, dip coating, or other coating methods. The outer balloon 272 can be formed from a Polyurethane material, a softer lower durometer Pebax than the outer balloon material, or a soft durometer Nylon, or Latex, or silicone, or other elastomeric polymeric material. The outer balloon 272 is bonded to the inner balloon 271 via the tie layer 273 or other bonding method at the ends of the outer waist. The tie layer 273 can be a thermally melted material that forms the bond between inner and outer balloon or it can be an adhesive material. One or more marker bands can be placed around the circumference of the balloon in the nadir or lowest diameter portion of the outer waist region or on either or both of the bulbs. The marker bands can be visualized using fluoroscopy or other means as described earlier.

The inner balloon 271 expands outwards at approximately 2 atm (range 1.5-3 atm) for expanding the stenotic aortic valve leaflets outwards. The outer balloon waist expands outwards from a diameter that is less than that of the aortic valve annulus to a diameter that makes definite contact with the annulus at a low pressure of approximately 0.5 to 1 atm (range 0.1-1.5 atm).

The method of use allows the inner balloon 271 to be first inflated via the inner inflation lumen 276 to cause dilation of the aortic valve leaflets at 2 atm and centering of the balloon 300 with the waist 300C of the balloon adjacent the aortic valve annulus 12. Secondly or simultaneously the outer balloon waist is inflated at 0.5 atm (range 0.1-1.5 atm) via the outer inflation lumen 275 to place the balloon waist 300C into contact with the aortic valve annulus. The marker band 278 located on the waist 300C of the outer balloon 272 assists in allowing accurate measurement of the aortic valve annulus 12 via fluoroscopy. The positioning of the aortic valve annulus along with its alignment with the axis of the aortic sinus and axis of the aortic annulus can also be determined by the positioning of the balloon 300 in the aortic root. The bulbs of the inner balloon 271 have a maximum inflation diameter that are approximately 5 mm larger than the inner balloon waist of the inner balloon 271 and therefore provide for alignment of the balloon axis with the axis of the aortic root. The outer waist has a maximum inflation diameter that is larger than the inner waist diameter and approximately equal to the inner balloon bulb diameter at a lower pressure of approximately 0.5-1.0 atm (range 0.1-1.5 atm).

Figure 43A:
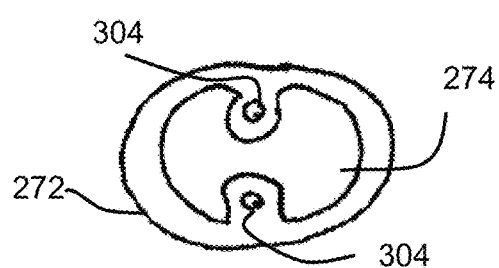
Figure 43B:
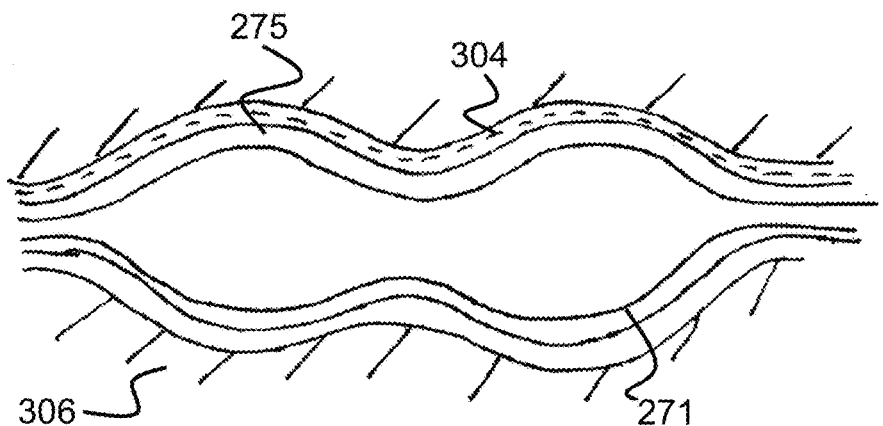
Figure 43C:
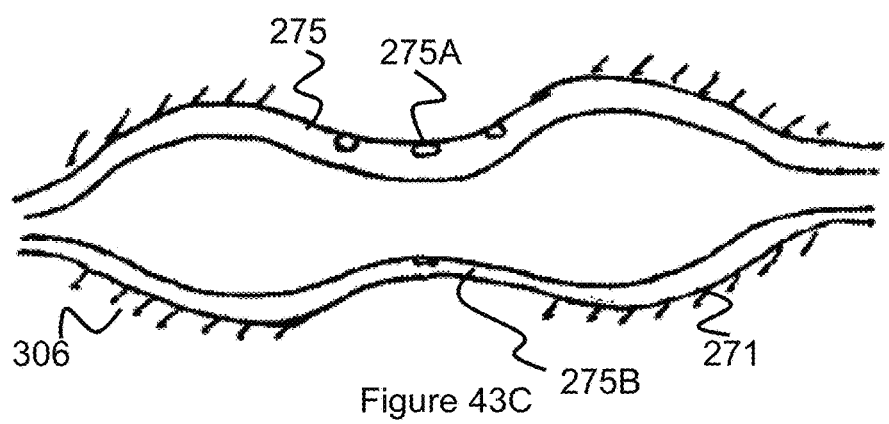

To form this balloon 300, the duel lumen or tri-lumen extrusion (or multi-lumen extrusion) has flexible mandrels 304 (for example NiTi or stainless steel) placed within the outer inflation lumen and outer evacuation lumen as shown in FIG. 43A. Alternately, the outer inflation lumen 274 can be filled with air or other fluid or maintained under pressure during the balloon blowing process within an external mold. Further alternately, the outer inflation lumen is simply maintained in an open condition exposed to air during the molding of the balloon. Other standard balloon blowing methods can be used, including application of temperature, pressure within the inner inflation lumen, and stretching of the tubing are performed during the balloon blowing process. The duel lumen tubing along with the mandrel 304 are placed within a mold 306 as shown in FIG. 43B and subjected to temperature and internal pressure within the inner balloon inflation lumen 271A. The balloon 300 is expanded against the surface of the mold 306 to form the bulbous shape. The mandrel 304 can then be removed from the balloon and openings 275A can be made into the outer balloon inflation lumen 275 at a location that corresponds to the waist region 300C as shown in FIG. 43C.

Alternately, the outer inflation lumen 275 and outer evacuation lumen 275B can be maintained during balloon molding by injecting a fluid (that is able to withstand the molding temperatures) into the inflation lumen 275 and evacuation lumen 275B and maintaining the fluid under pressure as the balloon is being molded. The outer inflation lumen can be filled with air or other fluid during the balloon molding process. A tie layer of a low melting temperature polymer is placed over the bulb portions of the inner balloon while masking the waist region (see FIG. 43C).

Figure 44A:
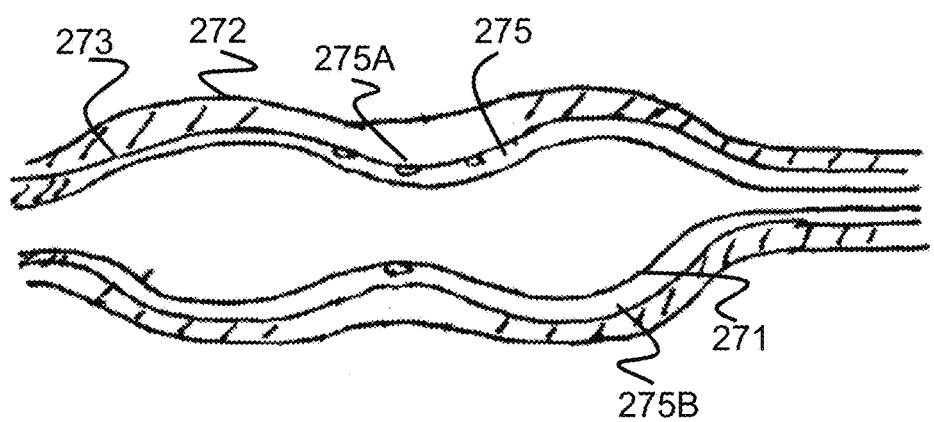

An outer balloon 272 is formed as a secondary step and placed over the inner balloon 271 as shown in FIG. 44A. The outer balloon can be formed via similar balloon molding step into a mold, or it can be applied as a coating directly onto the outside of the inner balloon 271 and tie layer 273. Alternately, the outer balloon waist can be formed separately as a portion of a balloon and bonded at each of its open ends to each bulb of the inner balloon 271. The outer balloon 272 is formed from an elastomeric polymer such a polyurethane, Pebax, Nylon, Silicone, Latex, or other elastomeric polymer used in the formation of medical device balloons. Upon placing the inner and outer balloon into a mold 306 and heating it, the outer balloon 306 will bond to the tie layer 273 at the bulbs of the inner balloon. Alternately, the outer balloon can be formed onto the inner balloon via any method that is available including coating the inner balloon with a coating of an elastomeric polymer.

Figure 44B:
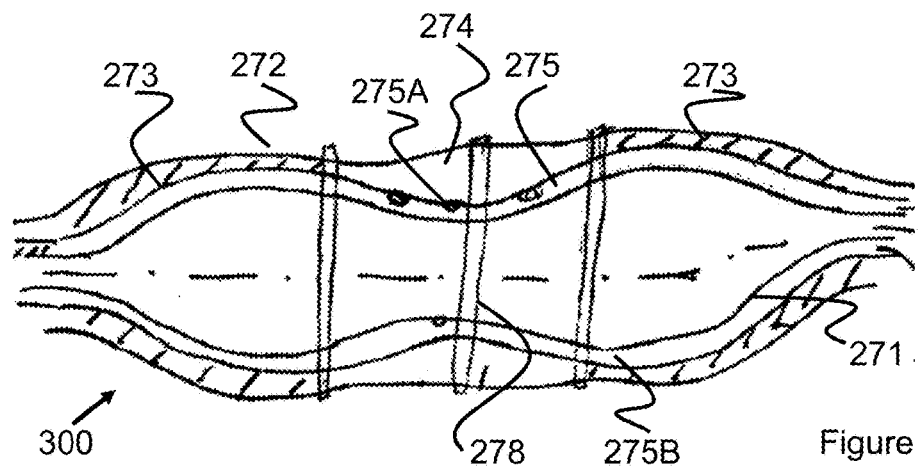

The outer inflation lumen 275 and outer evacuation lumens 275B have blocked lumens at the distal end of the balloon 300 to provide an enclosed space for the waist bladder. Upon inflation of the inner balloon to 2 atm the entire balloon forms a bulbous shape that will position itself across the aortic valve annulus. Further inflation of the outer balloon 275 to a low pressure, 0.5 to 1 atm (range 0.1-1.5 atm), enlarges the waist bladder to a large diameter as shown in FIG. 44B and places the waist into contact with the aortic annulus to allow accurate measurement of the aortic annulus in a stretch diameter that will not cause dissection of the annulus at low pressures of 0.5 to 1 atm (range 0.1-1.5 atm). Fluoroscopic measurement of the waist or visualization of the marker band 278 located in the waist will enhance the accuracy of the diameter measurement for the annulus.

A circumferential marker band 278 is also preferably located around one or more of the bulbs. The bulb marker bands 278 can be both circular in shape during balloon inflation and also provide an accurate diametric measurement of the balloon bulb. The round bulb marker band will appear oval when it is viewed from an oblique angle and will appear as a line when viewed under fluoroscopy from a direct frontal view perpendicular to the axis of the balloon. The bulb and waist marker bands 278 enable the alignment of the camera with the axis of the aortic sinus. Since the balloon aligns with the axis of the aortic sinus and the balloon waist positions itself adjacent the aortic annulus, the balloon provides both positional and alignment information to assist in the subsequent placement of a TAVR device. Comparison of the ratio of major to minor axis of the waist to the ratio of major to minor axis of the bulb allows determination of the ovality of the waist. Since the outer waist is in direct contact with the aortic valve annulus, the ovality of the annulus is determined from the ovality of the outer waist.

Inflation of the balloon embodiments having the waist bladder along with an inner balloon can be accomplished with a balloon inflation system comprised of two separate inflation devices or syringes if desired; one syringe can deliver a specified volume or pressure to the inner balloon and another syringe can deliver a specified pressure to the outer waist bladder as shown in FIGS. 38A, 39A, and 42A.

A pressure regulator can be used on one or both syringes to deliver a specific pressure, for example, to the inner balloon and a separate pressure to the outer waist bladder. The inner balloon can be inflated first, followed by inflation of the outer waist bladder. Alternately, both the inner balloon and outer waist bladder can be inflated at the same time or almost the same time such that the waist bladder is inflated almost immediately following the inflation of the inner balloon or at the same time.

Figure 45A:
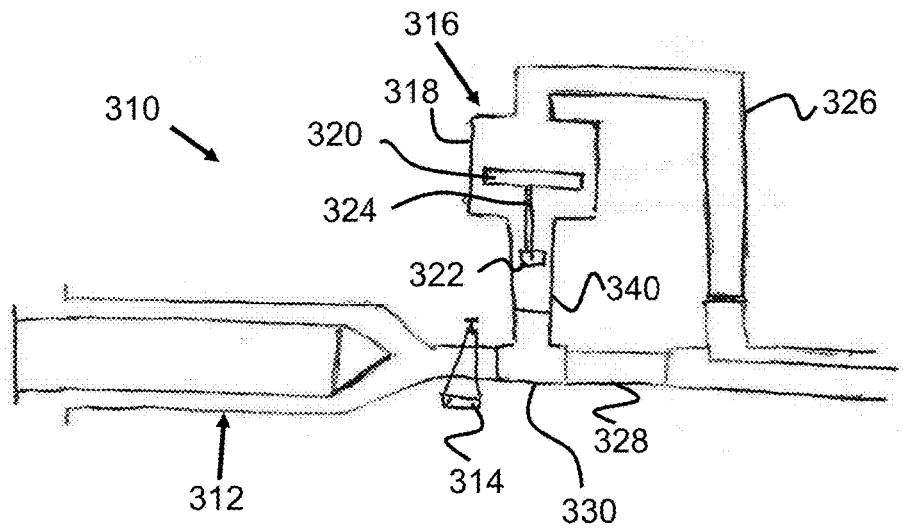

In another embodiment 310, a single syringe 312 can be used to inflate both the inner balloon 271 and the outer waist bladder 274 as presented in prior embodiments of the present invention, for example in FIGS. 44A-44C. FIG. 45A shows one embodiment 310 having the syringe 312 connected to a tee fitting 330 via a pressure regulator 314 (as described elsewhere in this specification). A direct leg or tube 328 extends from the tee fitting 330 and is connected directly to the inner balloon lumen 271A and thereby inflated it with fluid to the pressure generated by the syringe 312 or to a pressure that is regulated by a pressure regulator 314. Alternately, the inner balloon lumen 271A can be delivered a specified volume from the syringe 312.

The tee fitting 330 also connected to a pressure control cylinder 316. The pressure control cylinder 316 has a lower, small diameter cylinder 322 that is attached to an upper large diameter cylinder 320 via a connector member 324. The small diameter piston 322 is located in the small diameter cylinder 340, and a large diameter piston 320 is located in the large diameter cylinder 318. The small diameter piston 322 and larger diameter piston 320 are connected to each other via a solid connector or a fluid connection. The outlet of the large diameter cylinder 320 is connected to a low pressure leg or tube 326 that is connected to the outer balloon lumen 275 of the bladder balloon. For those catheters that have a balloon with an additional evacuation lumen 275B, the outer evacuation lumen 275B can also be connected to the low pressure leg 326 for inflation of the outer lumen 275. The pressure control cylinder 316 provides a lower pressure of media to the outer balloon lumen 275 than to the inner balloon lumen in accordance with the ratio of cross-sectional area of the small diameter cylinder to the area of the large diameter cylinder.

Figure 45B:
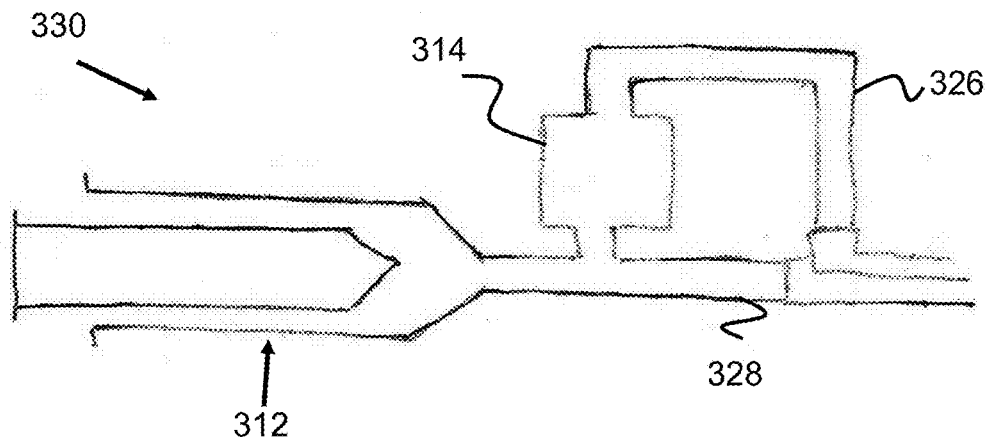
Figure 45C:
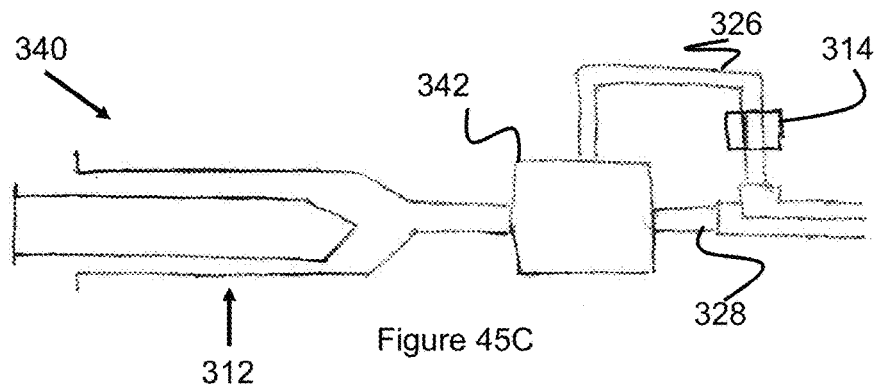

In yet another embodiment 330 a single inflation device or syringe is shown in FIG. 45B that delivers fluid volume to the inner balloon directly from the syringe via the direct leg to the inner balloon lumen and directs other fluid volume in parallel through a pressure regulator via the low pressure leg to the outer inflation lumen for inflation of the outer waist bladder at a lower pressure of approximately 0.5 atm (range 0.1-1.5 atm).

In still another embodiment 340 a spill-off control device 342 (as described elsewhere in this specification) allows fluid to flow via a direct leg 328 directly from the syringe 312 into the inner inflation lumen 274 to the inner balloon 271 until a specified pressure has been reached, for example, a pressure of 2 atm. Above this specified pressure any additional volume of media flows to the bladder inflation lumen 275. A pressure regulator 314 located in the low pressure leg 326 or attached to the spill-off control device 242 controls the media pressure delivered to the outer inflation lumen 275, which inflates the waist bladder 274 to a low pressure ranging from 0.25 to 0.5 1.0 atm, for example.

Figure 46:
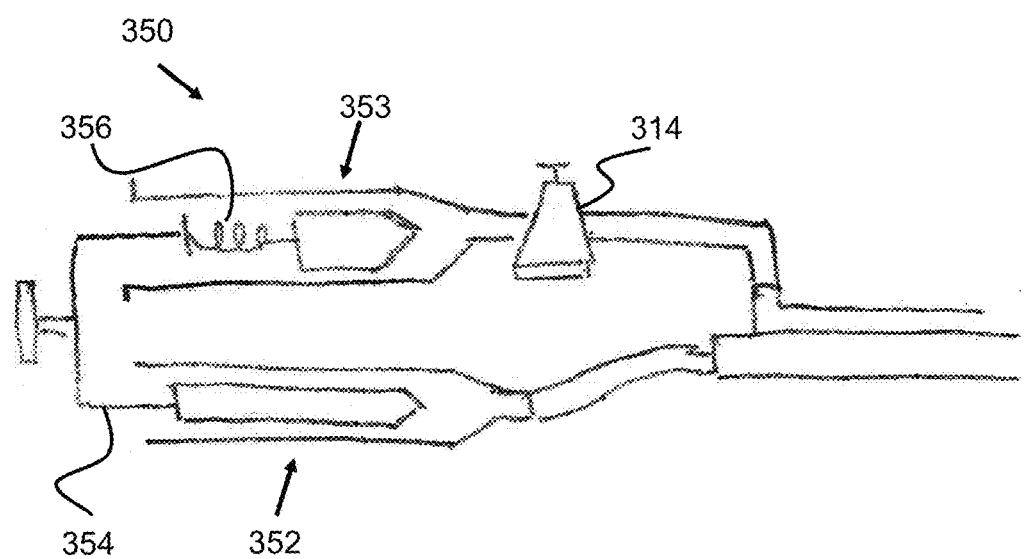

In yet another embodiment, an inflation device seen in FIG. 46 shows two syringes 352, 353 that are coupled together by a single plunger assembly 354 such that a single push of the full plunger 354 causes the first plunger 352 and the second plunger 353 to be depressed. The first plunger 352 delivers a specified volume of media to the inner balloon 271 to inflate it to a specified condition to dilate the aortic valve leaflets (approximately 2 atm). Media delivered by movement of the second plunger 353 is limited by a pressure regulator 314 (as described elsewhere in this specification) such that only a specified small pressure (i.e., 0.25-0.5 1.0 atm, for example) can be delivered via the low pressure leg to the outer inflation lumen 275 to the waist bladder 274. A spring 356, which is attached to the second plunger 353, allows the travel of the plunger 354 to compress the spring 356 and thereby deliver a smaller or lower pressure to the regulator 314.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A balloon catheter device for dilating stenotic tissue within human body, comprising:
    an elongated catheter shaft;
    a balloon assembly located at a distal end of said catheter shaft, said balloon assembly comprising:
        a first balloon forming a first balloon lumen and having an inflated shape forming a distal bulb, a proximal bulb, and a waist between said distal bulb and said proximal bulb; said waist having a smaller diameter than said distal bulb and said proximal bulb; and,
        a second balloon disposed over said first balloon, said second balloon being bonded to said distal bulb and said proximal bulb of said first balloon, and said second balloon being unattached to said waist of said first balloon, said first balloon lumen second balloon being independently inflatable.

2. The balloon catheter device of claim 1, further comprising a first radiopaque ring disposed at said waist and a second radiopaque ring disposed at either said proximal bulb or said distal bulb.

3. The balloon catheter device of claim 1, wherein said first balloon and said second balloon are formed from a multi-extrusion tubing.

4. The balloon catheter device of claim 1, further comprising an inflation lumen in fluid communication between said second balloon and being sealed from first balloon lumen.

5. The balloon catheter device of claim 1, further comprising a balloon inflation system, comprising:
    a fluid inflation assembly advancing fluid through said balloon inflation system;
    a pressure control assembly in communication with said fluid inflation assembly and limiting a pressure of said fluid advancing through said balloon inflation system.

6. The balloon catheter device of claim 5, wherein said balloon inflation system delivers a first pressure between about 1 and 3 atmospheres to said first balloon lumen and a second pressure between about 0.1 and 1 atmospheres to said second balloon.

7. The balloon catheter device of claim 5, wherein said balloon inflation system further comprises a pressure regulator valve releasing fluid from said balloon inflation system when said pressure of said fluid exceeds a predetermined level.

8. The balloon catheter device of claim 7, wherein said pressure regulator is a spill off valve.

9. The balloon catheter device of claim 1, wherein said first balloon is formed from a multi-extrusion tubing comprising said first balloon lumen and an inflation lumen in fluid communication between said second balloon and being sealed from first balloon lumen.

10. The balloon catheter device of claim 1, wherein said second balloon being unattached to said waist of said first balloon is formed from a semi-compliant material that allows said second balloon to expand to a larger diameter at a smaller pressure than said waist diameter of said first balloon.

11. A balloon catheter system for dilating tissue within a heart valve, comprising:
    an elongated catheter shaft;
    a balloon assembly located at a distal end of said catheter shaft, said balloon assembly comprising:
        a first balloon forming a first balloon lumen and having an inflated shape forming a distal bulb, a proximal bulb, and a waist between said distal bulb and said proximal bulb; said waist having a smaller diameter than said distal bulb and said proximal bulb; and,
        a second balloon disposed over said first balloon so as to form an outer waist lumen discrete from said first balloon lumen; said second balloon having an outer balloon waist portion that is radially expandable away from said waist of said first balloon; said outer balloon waist portion being formed from a semi-compliant material; said outer balloon waist portion forming a diameter that is larger than a proximal or distal bulb diameter at a pressure between 0.1 and 1.0 atmosphere;
        said second balloon being bonded to said proximal bulb and said distal bulb of said first balloon thereby limiting an upper diameter limit of said second balloon to a diameter equal to a diameter of said proximal bulb and said distal bulb;
        wherein said first balloon lumen and said second balloon are independently inflatable.

12. The balloon catheter system of claim 11, wherein proximal and distal portions of said first balloon and said second balloon are coupled together to form said outer waist lumen.

13. The balloon catheter system of claim 12, further comprising an inflation lumen in fluid communication between said outer waist lumen and being sealed from first balloon lumen.

14. The balloon catheter system of claim 13, wherein said inflation lumen is formed within said first balloon lumen.

15. The balloon catheter system of claim 14, further comprising a balloon inflation system, comprising:
    a fluid inflation assembly advancing fluid through said balloon inflation system;
    a pressure control assembly in communication with said fluid inflation assembly and limiting a pressure of said fluid advancing through said balloon inflation system.

16. The balloon catheter system of claim 15, wherein said balloon inflation system is configured to inflate said first balloon to a higher pressure than said second balloon.

17. The balloon catheter system of claim 16, wherein said balloon inflation system delivers a first pressure between about 1 and 3 atmospheres to said first balloon lumen and a second pressure between about 0.1 and 1 atmospheres to said outer waist lumen.

18. The balloon catheter system of claim 17, wherein said balloon inflation system further comprises a spill off valve.

* * * * *